US007727527B2

(12) United States Patent
Shelton

(10) Patent No.: US 7,727,527 B2
(45) Date of Patent: Jun. 1, 2010

(54) ANTI-NGF ANTIBODIES FOR THE THERAPEUTIC TREATMENTS

(75) Inventor: David L. Shelton, Oakland, CA (US)

(73) Assignee: Genentech, Inc., South San Francisco, CA (US)

( * ) Notice: Subject to any disclaimer, the term of this patent is extended or adjusted under 35 U.S.C. 154(b) by 526 days.

(21) Appl. No.: 10/479,872

(22) PCT Filed: May 9, 2002

(86) PCT No.: PCT/US02/15284

§ 371 (c)(1),
(2), (4) Date: Jun. 10, 2004

(87) PCT Pub. No.: WO02/096458

PCT Pub. Date: Dec. 5, 2002

(65) Prior Publication Data

US 2004/0219144 A1    Nov. 4, 2004

(51) Int. Cl.
*A61K 39/40* (2006.01)
(52) U.S. Cl. .................................. 424/141.1; 424/142.1
(58) Field of Classification Search ........................ None
See application file for complete search history.

(56) References Cited

U.S. PATENT DOCUMENTS

| 4,906,476 | A | * | 3/1990 | Radhakrishnan | 424/450 |
|---|---|---|---|---|---|
| 5,470,578 | A | * | 11/1995 | Aoki et al. | 424/450 |
| 7,425,329 | B2 | * | 9/2008 | Shelton et al. | 424/145.1 |
| 2001/0046959 | A1 | * | 11/2001 | Buchkovich et al. | 514/12 |
| 2004/0131615 | A1 | * | 7/2004 | Shelton et al. | 424/145.1 |
| 2004/0253244 | A1 | * | 12/2004 | Shelton et al. | 424/145.1 |
| 2006/0147450 | A1 | * | 7/2006 | Shelton | 424/145.1 |
| 2009/0252744 | A1 | | 10/2009 | Shelton et al. | |

FOREIGN PATENT DOCUMENTS

| WO | WO 00/73344 | | 9/1988 |
|---|---|---|---|
| WO | WO 01/78698 | * | 10/2001 |
| WO | WO 0178698 | * | 10/2001 |

OTHER PUBLICATIONS

Feldman et al., Transplant. Proc. 1998, 30, 4126-4127.*
Mestas et at J. of Immunology, 2004, 172, pp. 2731-238.*
Van Noort et al. International Review of Cytology, 1998).*
Ro et al Pain, 1999, v.79, pp. 265-274.*
Braun et al., E J. Immunol, 1998, v.28, pp. 3240-3251.*
Owens et al 1994 v.168, pp. 149-165.*
Shih et al., "Mutagenesis Identifies Amino-Terminal Residues of Nerve Growth Factor Necessart for Trk Receptor Binding and Biological Activity", The Journal of Biological Chemistry, vol. 269, No. 44, pp. 27679-27686 (1994) XP002062137, ISS: 0272-457X.
Torcia et al., "Nerve Growth Factor is an Autocrine Survival Factor for Memory B Lymphocytes", Cell, vol. 85, pp. 345-356 (1996), XP001153068, ISSN: 0092-8674.
Hongo et al., "Antibody Binding Regions on Human Nerve Growth Factor Identified by Homolog- and Alanine-Scanning Mutagenesis", Hybridoma, vol. 19, No. 3, pp. 215-227, 2000 (XP-002951932).
Shih et al., "Mutagenesis Identifies Amino-terminal Residues of Nerve Growth Factor Necessary for Trk Receptor Binding and Biological Activity", The Journal of Biological Chemistry, vol. 269, No. 44, Issue of Nov. 4, pp. 27679-27686, 1994 (XP-002062137).
Torcia et al., "Nerve Growth Factor Is an Autocrine Survival Factor for Memory B Lymphocytes", Cell, vol. 85, pp. 345.346, May 3, 1996 (XP-001153068).
Morrison, S. et al., "Chimeric Human Antibody Molecules: Mouse Antigen-Binding Domains with Human Constant Region Domains", Proc. Natl. Acad. Sci. USA, vol. 81, pp. 6851-6855 (1984).
Holliger, P. et al., ""Diabodies": Small Bivalent and Bispecific Antibody Fragments", Proc. Natl. Acad. Sci. USA, vol. 90, pp. 6444-6448 (1993).
Braun et al., "Role of Nerve Growth factor in a Mouse Model of Allergic Airway Inflammation and Asthma" Eur. J. Immunol. 1998, 28:3240-3251.
Braun et al., "Neurotrophins: A Link Between Airway Inflammation and Airway Smooth Muscle Contractility in Asthma?" Int. Arch Allergy Immunol. 1999;118;163-065.
Garaci et al. "Nerve Growth Factor is an autocrine factor essential for the survival of macrophages infected with HIV" *Proc. Natl. Acad. Sci.* 96(24):14013-14018 (1999).

* cited by examiner

*Primary Examiner*—Michail A Belyavskyi
(74) *Attorney, Agent, or Firm*—Jennifer L. Elliott; James A. Fox; Ginger R. Dreger

(57) ABSTRACT

The present invention relates generally to methods of using anti-NGF antibodies in the treatment of various NGF-related disorders, including asthma, arthritis and psoriasis. The methods are effective in treating these disorders in a patient without having a significant adverse effect on the immune system of the patient.

12 Claims, 29 Drawing Sheets

FIG. 1

Identification of MAb Binding Regions by Homolog-Scanning Mutagenesis

| *Mutant Name*[a] | *NGF→NT3* mutations *introduced*[b] | *Region mutated*[c] | *908*[d] | *909* | *911* | *912* | *938* | *14.14* |
|---|---|---|---|---|---|---|---|---|
| Wildtype | None | | (+++) | (+++) | (+++) | (+++) | (+++) | (+++) |
| 6 | S1Y, S2A, S3E, P5K, I6S, F7S | N-terminal | (+++) | (+++) | (+++) | (+++) | (++) | (-) |
| 20 | V18E, V20L, G23T | Pre-V-1 (β-sheet A) | (+++) | (++) | (+++) | (+++) | (++) | (+++) |
| 19 | T26S, T27S, T29I, K32R, K34H, E35Q | V-1 (β-hairpin turn A'-A") | (+/++) | (+++) | (++) | (+/++) | (++) | (+++) |
| 12 | V42I, N43K, 144T, N45G, V48P, F49V | V-2 (β-hairpin turn A'''-B) | (-) | (+++) | (+++) | (+++) | (+++) | (+++) |
| 7 | R59K, D60E, P61A, N62R, D65K, S66N | V-3 (β-reverse turn B-C) | (+++) | (-) | (+++) | (+++) | (+++) | (+++) |
| 16 | Y79Q, T81K, T83S, H84Q, F86Y, K88R | V-4 (β-sheet C) | (+++) | (+++) | (++) | (+++) | (+++) | (+++) |
| 8 | M92S, D93E, G94N, +N94/95, Q96L, A97V, A98G | V-5 (β-hairpin turn C-D) | (++) | (+++) | (+++) | (++) | (+++) | (+++) |
| 23 | A116I, V117G, R119T, R120(-) | C-terminal | (+++) | (+++) | (+++) | (+++) | (+) | (+++) |
| Epitope region | | | V-2 | V-3 | V-1, V-4 | V-1, V-5 | C-term. | N-term. |

[a]Mutant names were assigned in the order that they were prepared. [b]Residues of hNGF were replaced by nonhomologous residues of hNT3. The mutations are based on residues (one-letter symbol and position number) replaced by the residue immediately following the position number indicated.
[c]Each of the variable regions of hNGF was mutated to determine the binding specificity of each MAb. [d]The relative binding of each of six MAbs to the NGF/NT3 homolog-scan mutants is compared to the binding of wildtype hNGF: (-), <10%; (+), 10-30%; (++), 30-60%; (+++), 60-100%. The $EC_{50}$ of each MAb for binding to hNGF is: MAb 908, $1.8 \times 10^{-10}$ M; MAb 909, $1.8 \times 10^{-10}$ M; MAb 911, $3.7 \times 10^{-10}$ M; MAb 912, $1.8 \times 10^{-10}$ M; MAb 938, $7.4 \times 10^{-10}$ M; MAb 14.14, $5.9 \times 10^{-10}$ M.

FIG 5

Summary of MAb Epitope Mapping Results

| *MAb* | *NGF binding regions point mutations* | *TrkA binding site NGF/TrkA STRUCTURE*[a] | *p75 binding site NGF-3 mutagenesis*[b] | *TrkA blocking activity* | *p75 blocking activity* |
|---|---|---|---|---|---|
| 908 | M92, M97, E41, N46 | No | No | (+/-) | (+/-) |
| 909 | R59, R69 | No | Yes | (-) | (++) |
| 911 | Various | Yes | Yes | (++) | (++) |
| 912 | Various | No | Yes | (++) | (++) |
| 938 | L112/S113 | Yes | Yes | (++) | (+) |
| 14.14 | H4, P5 | Yes | No | (+/-) | (-) |

FIG. 17

Anti-NGF does not inhibit the humoral immune response to dust mite antigen ically induced arthritis in animal models (see e.g. Levine, J., *Science* 226:547-549 (1984)). NGF has been shown to affect mast cell degranulation (Bruni at al., *FEBS Lett.* 138:190-193 (1982)) and substance P release (Donnerer et al., *Neurosci.* 49:693-698 (1992)), implicating it in the pathogenesis of arthritis.

ANTI-NGF ANTIBODIES FOR THE THERAPEUTIC TREATMENTS

BACKGROUND OF THE INVENTION

1. Field of the Invention

The present invention relates generally to methods of using anti-NGF antibodies in the treatment of various NGF-related disorders, including asthma, arthritis and psoriasis. The methods are effective in treating these disorders in a patient without having a significant adverse effect on the immune system of the patient.

2. Description of the Related Art

Nerve Growth Factor (NGF)

Nerve growth factor (NGF) was the first neurotrophin to be identified, and its role in the development and survival of both peripheral and central neurons has been well characterized. NGF has been shown to be a critical survival and maintenance factor in the development of peripheral sympathetic and embryonic sensory neurons and of basal forebrain cholinergic neurons (Smeyne et al., *Nature* 368:246-249 (1994); Crowley et al., *Cell* 76:1001-1011 (1994)). NGF upregulates expression of neuropeptides in sensory neurons (Lindsay and Harmer, *Nature* 337:362-364 (1989)) and its activity is mediated through two different membrane-bound receptors. The TrkA tyrosine kinase receptor mediates high affinity binding and the p75 receptor, which is structurally related to other members of the tumor necrosis factor receptor family, mediates low affinity binding (Chao et al., *Science* 232:518-521 (1986)).

In addition to its effects in the nervous system, NGF has been increasingly implicated in processes outside of the nervous system. For example, NGF has been shown to enhance vascular permeability (Otten et al., *Eur. J. Pharmacol.* 106:199-201 (1984)), enhance T- and B-cell immune responses (Otten et al., *Proc. Natl. Acad. Sci. U.S.A.* 86:10059-10063 (1989)), induce lymphocyte differentiation and mast cell proliferation and cause the release of soluble biological signals from mast cells (Matsuda et al., *Proc. Natl. Acad. Sci. U.S.A.* 85:6508-6512 (1988); Pearce et al., *J. Physiol.* 372:379-393 (1986); Bischoff et al., *Blood* 79:2662-2669 (1992); Horigome et al., *J. Biol. Chem.* 268:14881-14887 (1993)).

NGF is produced by a number of cell types including mast cells (Leon et al., *Proc. Natl. Acad. Sci. U.S.A.* 91:3739-3743 (1994)), B-lymphocytes (Torcia et al., *Cell* 85:345-356 (1996), keratinocytes (Di Marco et al., *J. Biol. Chem.* 268:22838-22846)) and smooth muscle cells (Ueyama et al., *J. Hypertens.* 11:1061-1065 (1993)). NGF receptors have been found on a variety of cell types outside of the nervous system. For example, TrkA has been found on human monocytes, T- and B-lymphocytes and mast cells.

Consistent with a non-neuronal role for NGF, an association between increased NGF levels and a variety of inflammatory conditions has been observed in human patients as well as in several animal models. These include systemic lupus erythematosus (Bracci-Laudiero et al., *Neuroreport* 4:563-565 (1993)), multiple sclerosis (Bracci-Laudiero et al., Neurosci. Lett. 147:9-12 (1992)), psoriasis (Raychaudhuri et al., *Acta Derm. Venereol.* 78:84-86 (1998)), arthritis (Falcini et al., *Ann. Rheum. Dis.* 55:745-748 (1996)) and asthma (Braun et al., *Eur. J. Immunol.* 28:3240-3251 (1998)). Chronic inflammatory conditions such as these are a significant public health problem. For instance, it is estimated that arthritis affects 37.9 million people in the United States alone. Current therapies for treating these conditions are severely limited. An understanding of the role NGF plays in these diseases may provide new methods for treating them.

A correlation between stress and psoriasis has been observed. Based on this correlation and the symmetry of the cutaneous lesions that accompany the disease, a relationship with the nervous system has been proposed (Raychaudhuri et al., *Acta Derm. Venercol.* 78:84-86 (1998)). In particular, neuropeptides have been suggested to play a role in the pathogenesis of psoriasis. Investigators have reported an increased number of terminal cutaneous nerves along with upregulation of one or more of the neuropeptides, such as substance P (SP), vasoactive intestinal polypeptide (VIP) and CGRP. NGF plays a role in regulating innervation in the skin and also is known to upregulate neuropeptides, suggesting that increased NGF levels may be responsible for the upregulation of neuropeptides and the increased cutaneous innervation seen with psoriasis. In fact, increased expression of NGF has been observed in psoriatic keratinocytes (Raychaudhuri et al., *Acta Derm. Venercol.* 78:84-86 (1998)). It has been suggested that while NGF normally serves as a survival factor for keratinocytes, overexpression of NGF prevents normal cell death, leading to psoriasis (Pincelli at al., *J. Derm. Sci.* 22:71-79 (2000)).

A number of studies have indicated that neuropeptides such as substance P (SP) and biologically active compounds released from mast cells, such as histamine, also play a role in both naturally occurring arthritis in humans and experimentally induced arthritis in animal models (see e.g. Levine, J., *Science* 226:547-549 (1984)). NGF has been shown to affect mast cell degranulation (Bruni at al., *FEBS Lett.* 138:190-193 (1982)) and substance P release (Donnerer et al., *Neurosci.* 49:693-698 (1992)), implicating it in the pathogenesis of arthritis.

Consistently, an elevated level of NGF in peripheral tissues is associated with both hyperalgesia and inflammation and has been observed in a number of forms of arthritis. The synovium of patients affected by rheumatoid arthritis expresses high levels of NGF while in non-inflamed synovium NGF has been reported to be undetectable (Aloe et al., *Arch. Rheum.* 35:351-355 (1992)). Similar results were seen in rats with experimentally induced rheumatoid arthritis (Aloe et al., *Clin. Exp. Rheumatol.* 10:203-204 (1992)). Elevated levels of NGF have been reported in transgenic arthritic mice along with an increase in the number of mast cells. (Aloe et al., *Int. J. Tissue Reactions-Exp. Clin. Aspects* 15:139-143 (1993)). However, purified NGF injected into the joint synovium of normal rats does not induce knee joint inflammation, suggesting that NGF does not play a causative role in arthritis (Aloe et al., *Growth Factors* 9:149-155 (1993)).

High NGF levels have been associated with allergic inflammation and it has been suggested that this is related to mast cell degranulation (Bonini et al., *Proc. Natl. Acad. Sci. U.S.A.* 93:10955-10960 (1996)).

Elevated NGF levels are also observed in both allergic and non-allergic asthma (Bonini et al., supra). Mast cells, eosinophils and T-lymphocytes have all been proposed to play a role in this inflammatory disease and the correlation between NGF serum levels and total IgE antibody titers suggests that NGF contributes to the inflammatory immune response. Allergen induced airway inflammation has been associated with increased local production of NGF in both mice and humans (Braun et al., *Int. Arch. Allergy Immunol.* 118:163-165 (1999)).

NGF has been shown to regulate the development of increased airway hyperactive response, a hallmark of bronchial asthma (Braun et al., *Eur. J. Immunol.* 28:3240-3251

(1998)). Indeed, in one study, treatment of allergen-sensitized mice with anti-NGF antibody prevented the development of airway hyperresponsiveness following local allergen challenge (Braun et al., *Int. Arch. Allergy Immunol.* 118:163-165 (1999)).

Despite the promising results obtained in mice, reported adverse effects of neutralizing anti-NGF antibodies on the immune system have raised serious questions about the feasibility of using anti-NGF antibodies as a therapeutic in the prevention or treatment of asthma or other diseases or disorders in human patients. In particular, Torcia at al., *Cell* 85:345-356 (1996) identified NGF as an autocrine survival factor for memory B lymphocytes, and demonstrated that in vivo administration of neutralizing anti-NGF antibodies caused a depletion of memory B-cells and abolished secondary antigen-specific immune responses in mice. Garaci et al., *Proc. Natl. Acad. Sci. USA* 96:14013-14018 (1999) reported that NGF is an autocrine survival factor that rescues human monocytes/macrophages from the cytopathic effect caused by HIV infection. This report, along with the findings of Torcia et al., supra would suggest that anti-NGF antibodies have the potential of compromising the immune system of the subject treated.

SUMMARY OF THE INVENTION

The present invention is based on the unexpected finding that in vivo administration of a therapeutically effective amount of an anti-NGF monoclonal antibody (antibody 911) had no adverse effect on the immune system in an experimental mouse model of allergy. Accordingly, this and related antibodies hold great promise in the treatment of NGF-associated disorders, including asthma, in human patients.

In one aspect, the invention concerns a method of controlling an NGF-related disorder in a human patient by administering to the patient an effective amount of an anti-human NGF (anti-hNGF) monoclonal antibody that is capable of binding hNGF with an affinity in the nanomolar range, and inhibiting the binding of hNGF to human TrkA (hTrkA) in vivo, wherein the antibody has no significant adverse effects on the immune system of the patient.

In one embodiment the binding affinity of the antibody to hNGF is preferably about 0.10 to about 0.80 nM, more preferably about 0.15 to about 0.75 nM and even more preferably about 0.18 to about 0.72 nM.

In another embodiment, the antibody binds essentially the same hNGF epitope as an antibody selected from the group consisting of MAb 911, MAb 912 and MAb 938, more preferably the same epitope as MAb 911.

In yet another embodiment the antibody is able to cross react with murine NGF (muNGF).

The antibody may also be an antibody fragment, preferably an antibody fragment selected from the group consisting of Fab, Fab', F(ab')$_2$, Fv fragments, diabodies, single chain antibody molecules and multispecific antibodies formed from antibody fragments, and more preferably a single-chain Fv (scFv) molecule.

In another embodiment the antibody is chimeric. It may also be humanized or human.

In yet another embodiment the antibody is bispecific. The bispecific antibody may have an anti-IgE specificity.

The NGF-related disorder that is controlled is preferably not associated with the effect of NGF on the neuronal system.

In one embodiment the NGF-related disorder is an inflammatory condition, preferably selected from the group consisting of asthma, arthritis, multiple sclerosis, lupus erythematosus and psoriasis.

In a preferred embodiment the condition is asthma. In another embodiment the condition is arthritis, preferably rheumatoid arthritis. In yet another embodiment the condition is psoriasis.

In yet a further embodiment, the antibody is administered in combination with another therapeutic agent for the treatment of an inflammatory condition. Thus the antibody may be administered in combination with another therapeutic agent for the treatment of asthma. In one embodiment the antibody is administered with a corticosteroid, preferably beclomethsone diproprionate (BDP). In another embodiment the antibody is administered with an anti-IgE antibody, such as rhuMAb-E25 or rhuMAb-E26. For the treatment of rheumatoid arthritis, the antibody may be administered in combination with an anti-TNF antibody or an antibody or immunoadhesin specifically binding a TNF receptor.

In another aspect, the invention concerns a pharmaceutical composition comprising a chimeric, humanized or human anti-human NGF monoclonal antibody capable of binding hNGF with an affinity in the nanomolar range and inhibiting the binding of hNGF to human TrkA in vivo, wherein the antibody has no significant adverse effects on the immune system of a patient, in combination with a pharmaceutically acceptable carrier. The antibody in the pharmaceutical composition may be an antibody fragment, preferably an antibody fragment selected from the group consisting of Fab, Fab', F(ab')$_2$, Fv fragments, diabodies, single-chain antibody molecules and multispecific antibodies formed from antibody fragments.

In one embodiment the antibody is a bispecific antibody. The bispecific antibody may be capable of specific binding to native human IgE or native human TNF or a native human TNF receptor.

In another embodiment the pharmaceutical composition further comprises another pharmaceutically active ingredient, such as an ingredient suitable for the treatment of an inflammatory condition. The inflammatory condition is preferably one selected from the group consisting of asthma, multiple sclerosis, arthritis, lupus erythematosus and psoriasis. In one embodiment the inflammatory condition is asthma. In another embodiment the inflammatory condition is arthritis, preferably rheumatoid arthritis. In yet another embodiment the inflammatory condition is psoriasis.

In another aspect, the present invention relates to an article of manufacture comprising a container, a pharmaceutical composition comprising a chimeric, humanized or human anti-human NGF monoclonal antibody capable of binding hNGF with an affinity in the nanomolar range and inhibiting the binding of hNGF to human TrkA in vivo, wherein the antibody has no significant adverse effects on the immune system of a patient, in combination with a pharmaceutically acceptable carrier, and instructions for using the composition of matter to control an NGF-related disorder in a human patient.

In one embodiment the article of manufacture comprises a further pharmaceutically active ingredient, preferably suitable for the treatment of an inflammatory condition. The inflammatory condition is preferably selected from the group consisting of asthma, multiple sclerosis, arthritis, lupus erythematosus and psoriasis.

BRIEF DESCRIPTION OF THE DRAWINGS

FIG. 1 summarizes the ability of six anti-NGF MAbs to bind to NGF/NT-3 chimeric mutants. The relative binding of each MAb to the NGF/NT3 mutants is compared to the binding of wildtype hNGF: (−), <10%; (+), 10-30%; (++), 30-60%; (+++), 60-100%. The $EC_{50}$ of each MAb for binding to hNGF is: MAb 908, $1.8\times10^{-10}$ M; MAb 911, $3.7\times10^{-10}$ M; MAb 912, $1.8\times10^{-10}$ M; MAb 938, $7.4\times10^{-10}$ M; MAb 14.14, $5.9\times10^{-10}$ M.

FIG. 2A shows binding of MAb 908 to wild type and mutant NGF.

FIG. 2B shows binding of MAb 909 to wild type and mutant NGF.

Figure 2A:
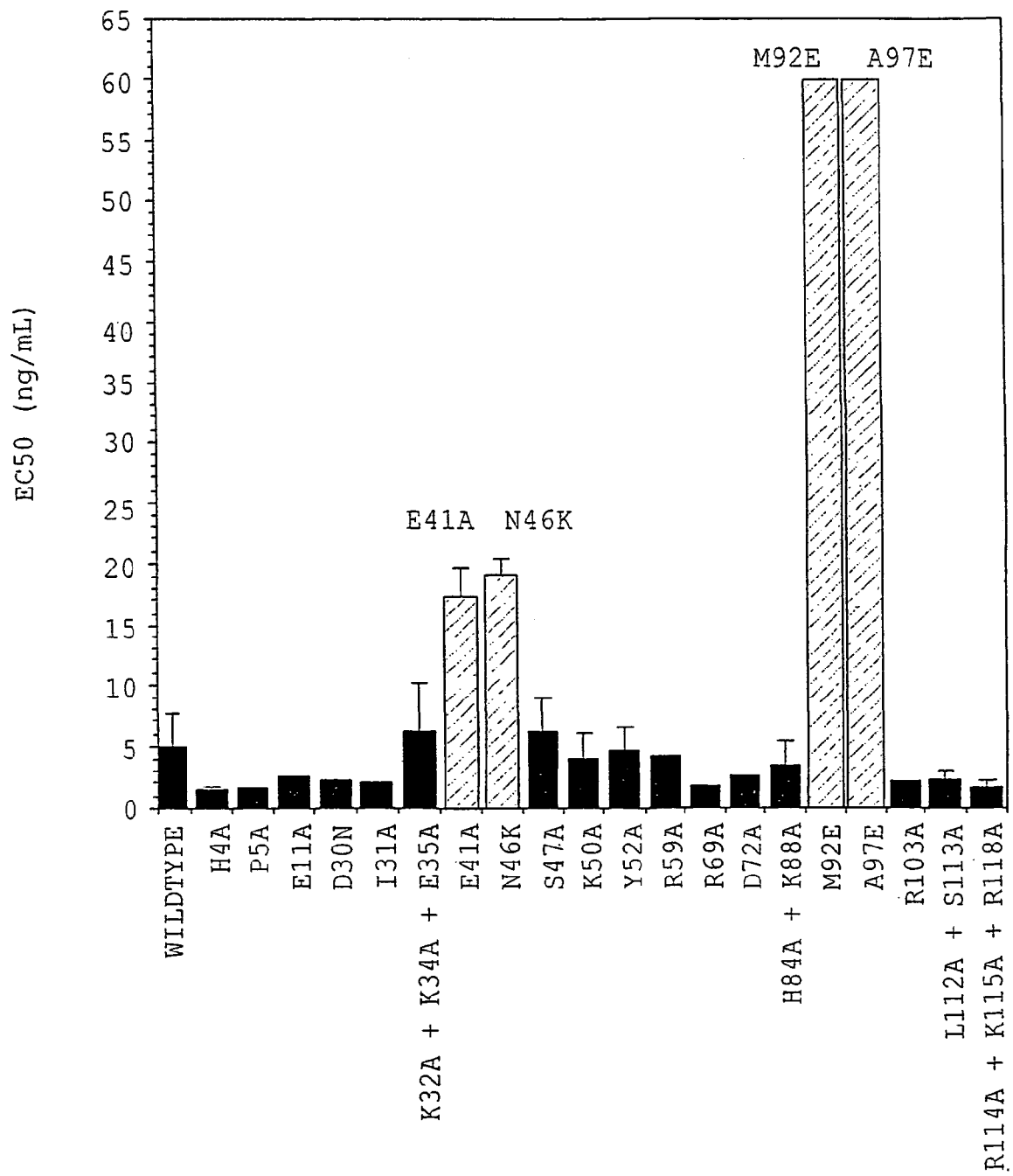
FIGS. 2A-F shows the binding of MAbs to wild type and mutant hNGF. The average $EC_{50}$ values for each mutant obtained in 2 to 5 independent ELISA runs were compared to $EC_{50}$ values obtained for wild type NGF binding. $EC_{50}$ values were determined by linear regression analysis (unweighted) using the Kaleidagraph software program (Abelbeck Software). Mutants resulting in at least a two-fold reduction in MAb binding are designated by striped bars, and the contributing residues are labeled.
Figure 2B:
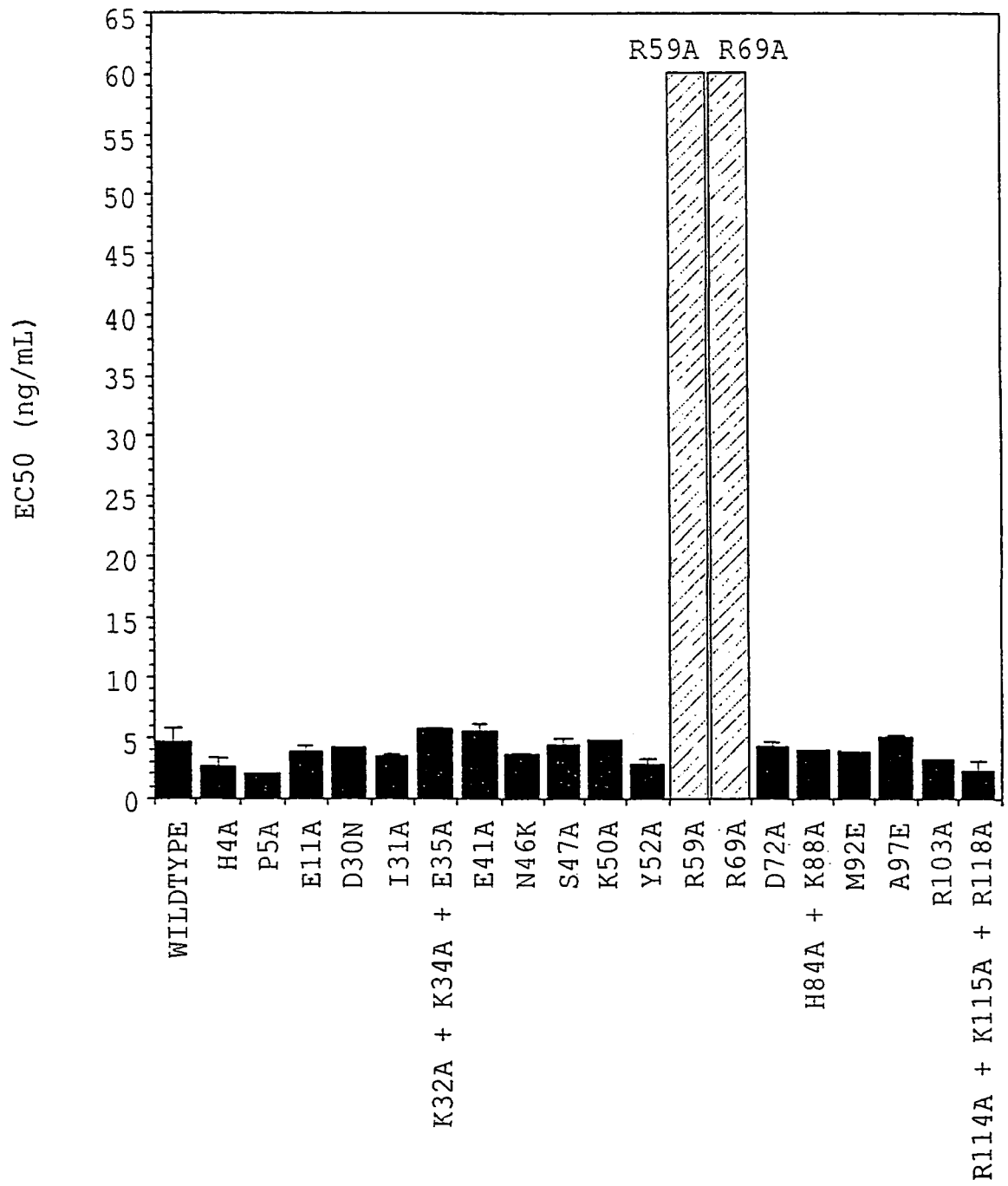
Figure 2C:
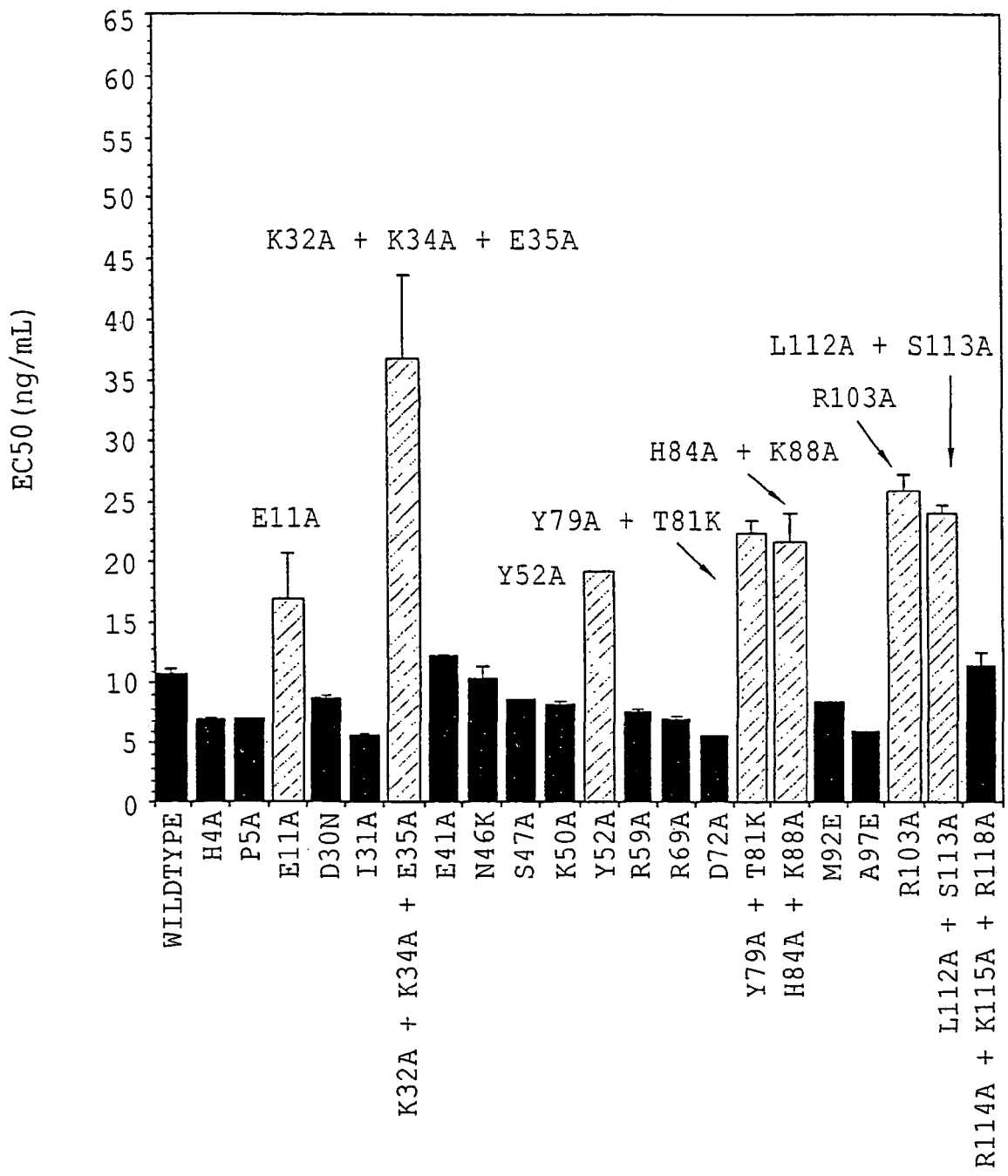
Figure 2D:
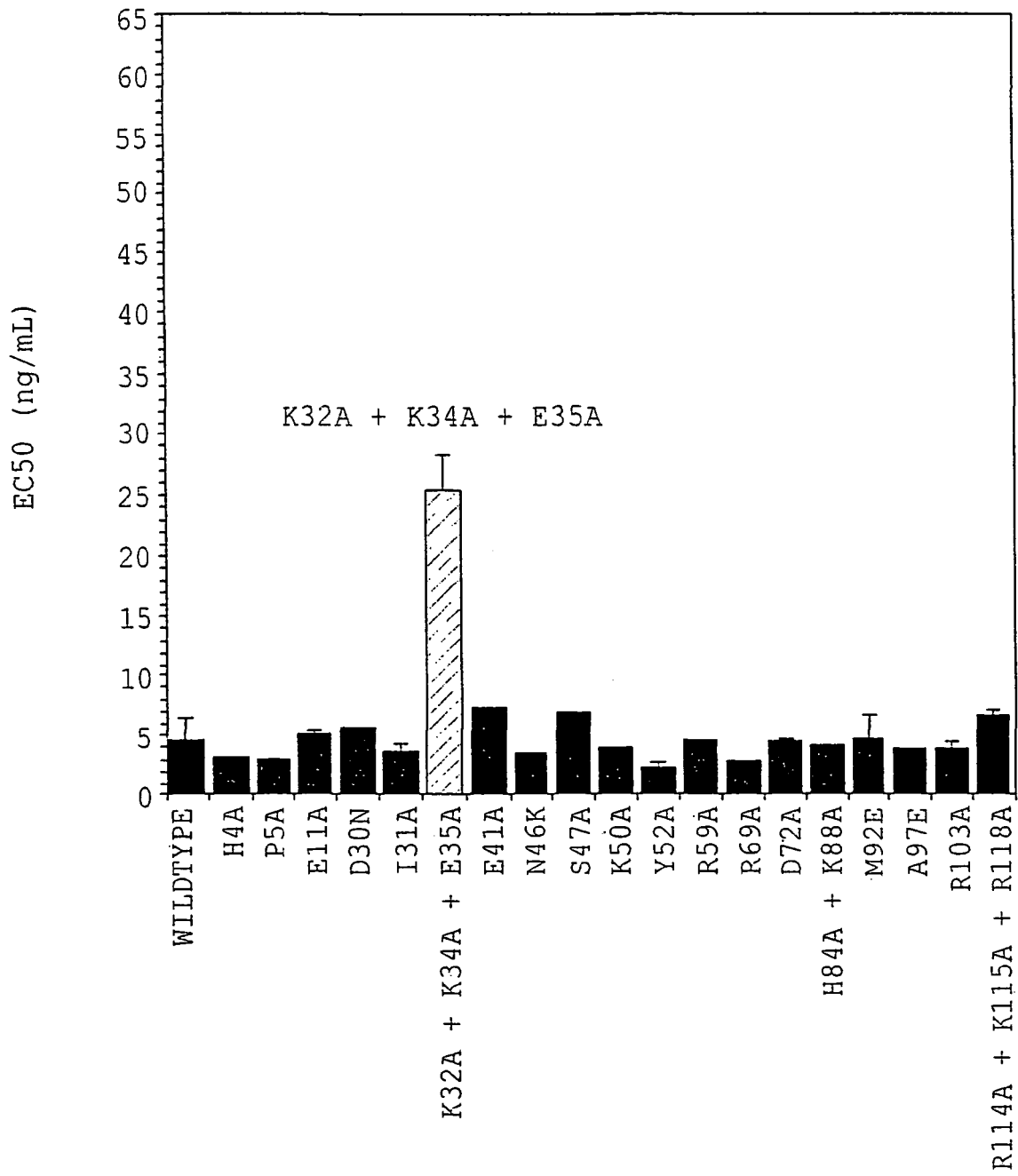
Figure 2E:
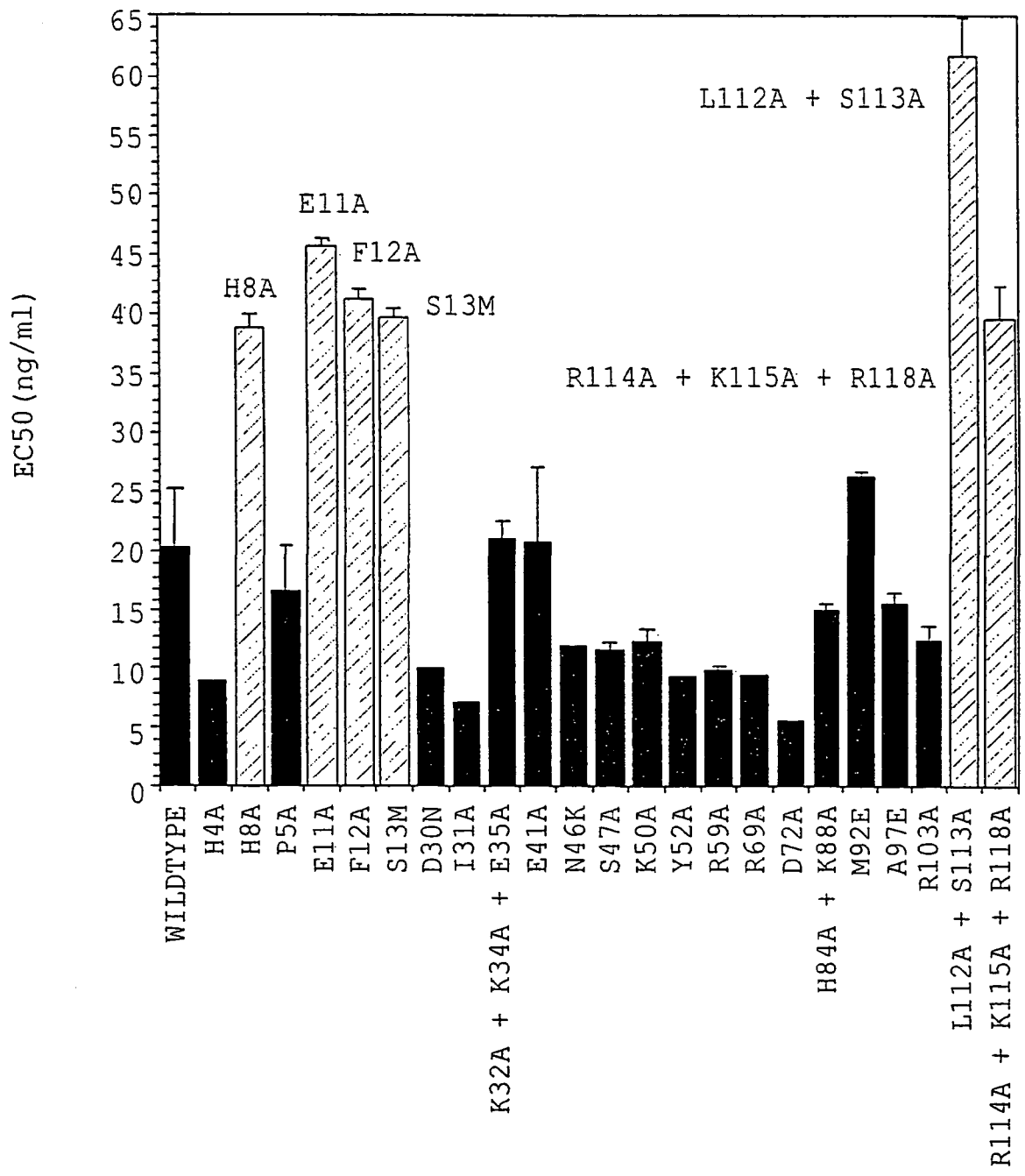
Figure 2F:
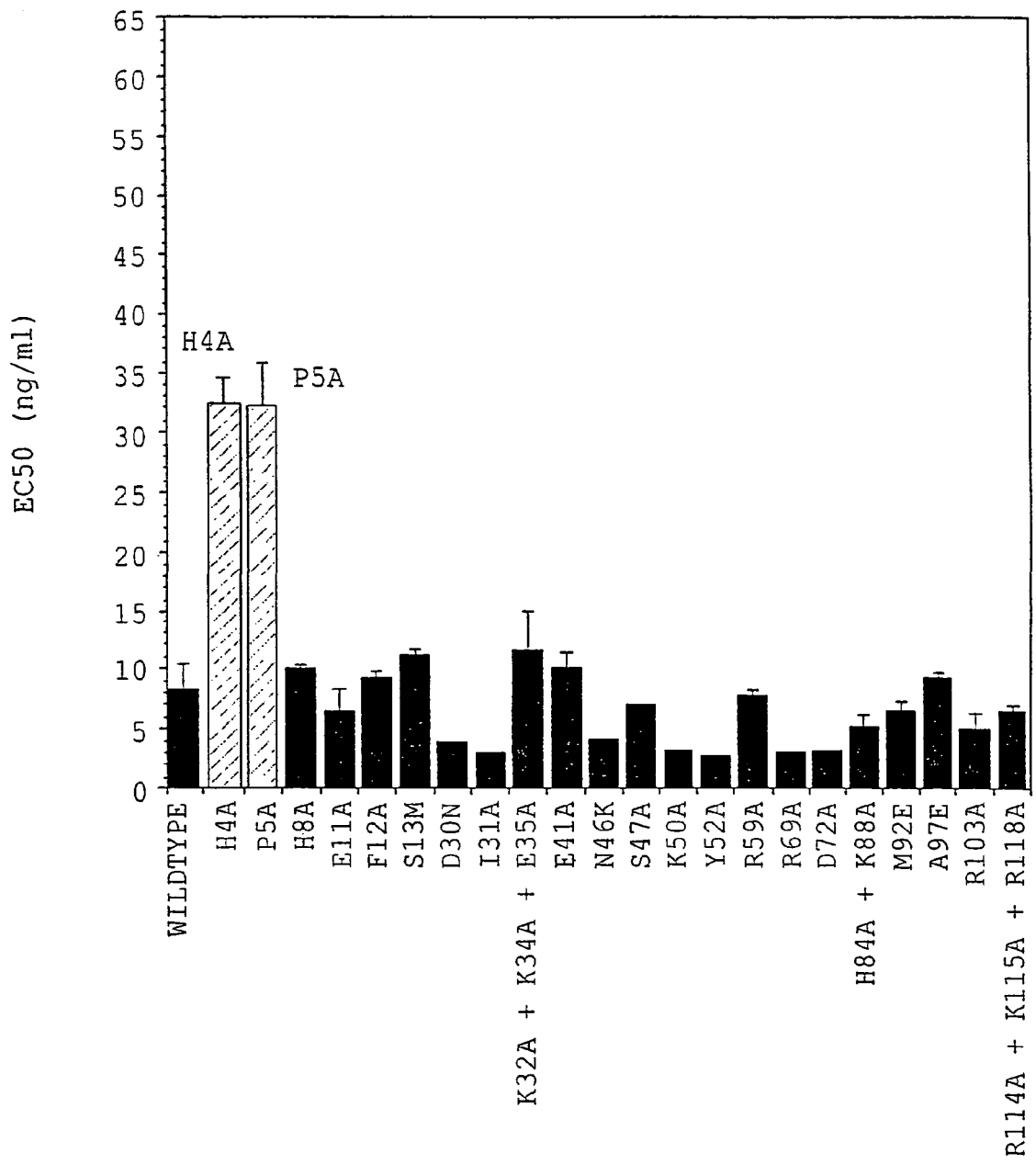

FIG. 2C shows binding of MAb 911 to wild type and mutant NGF.

FIG. 2D shows binding of MAb 912 to wild type and mutant NGF.

FIG. 2E shows binding of MAb 938 to wild type and mutant NGF.

FIG. 2F shows binding of MAb 14.14 to wild type and mutant NGF.

FIGS. 3A-F presents molecular models of MAb epitopes on NGF for anti-NGF MAbs 908, 909, 911, 912, 938 and 14.14, respectively. The light and medium gray designations differentiate each monomer of NGF, and residues identified by ELISA that affect MAb binding are shown in black. Each of the variable regions is labeled in FIG. 3A.

FIGS. 4A and B show immunoblot analysis of anti-NGF MAb binding to non-reduced hNGF (A) and reduced hNGF (B). Molecular weight markers are visible in the first lane. Buffer and a negative control antibody are shown in lanes 2 and 3, respectively. Under non-reducing conditions, purified hNGF ran as a triplet set of bands, which appear to correspond to monomeric, dimeric and partially processed dimeric hNGF.

FIG. 5 summarizes the MAb epitope mapping results.

FIG. 6 shows that anti-NGF MAbs inhibited binding of hNGF to a TrkA-IgG receptor immunoadhesin.

FIG. 7 shows the ability of anti-NGF MAbs to inhibit binding of hNGF to a p75-IgG immunoadhesin.

FIG. 8 shows the ability of anti-NGF MAbs to inhibit binding of hNGF to the TrkA extracellular domain expressed on transfected CHO cells. Inhibition of tyrosine phosphorylation was measured by ELISA using an antiphophotyrosine MAb.

FIG. 9 shows the ability of anti-NGF MAbs to inhibit the survival effects of hNGF on embryonic rat dorsal root ganglion neurons. Maximum survival was based on the signal obtained with NGF alone, and maximal inhibition determined by the signal obtained with the addition of saturating concentrations of soluble TrkA-IgG.

FIG. 10 demonstrates that treatment with anti-NGF MAb 911 non-significantly increases the immune response to ovalbumin.

FIG. 11 shows that following immunization with chicken gamma-globulin, treatment with anti-NGF MAb 911 non-significantly reduces the immune response.

FIG. 12 shows that treatment with anti-NGF MAb 911 blocks NGF induced thermal hyperalgesia.

FIG. 13 shows that in sensitized C57/BL6 mice (SN), treatment with anti-NGF MAb 911 inhibits airway hyperreactivity following challenge with inhaled dust mite antigen.

FIG. 14 shows that in sensitized C57/BL6 mice (SN), treatment with anti-NGF MAb decreases infiltration of white blood cells, lymphocytes and eosinophils into BAL following challenge with inhaled dust mite antigen.

FIG. 15 shows that while cellular infiltration into BAL is decreased in anti-NGF MAb treated sensitized mice, the proportion of eosinophils remains high.

FIG. 16 shows that treatment with anti-NGF MAb 911 attenuates the increase of IL-13 in BAL following antigen challenge.

FIG. 17 demonstrates that despite its ability to decrease the inflammatory response to allergen, treatment with anti-NGF MAb does not decrease the humoral immune response as measured by total serum immunoglobulin titer to dust mite.

FIG. 18 shows that treatment with anti-NGF MAb also does not decrease the total serum level of IgE.

FIG. 19 shows that treatment with NGF increases the levels of CGRP in the trigeminal ganglion, while treatment with anti-NGF MAb produces a decrease in CGRP levels.

DETAILED DESCRIPTION OF THE PREFERRED EMBODIMENT

A. Definitions

Unless defined otherwise, technical and scientific terms used herein have the same meaning as commonly understood by one of ordinary skill in the art to which this invention belongs. See, e.g. Singleton et al., *Dictionary of Microbiology and Molecular Biology* 2nd ed., J. Wiley & Sons (New York, N.Y. 1994); Sambrook et al., *Molecular Cloning, A Laboratory Manual*, Cold Springs Harbor Press (Cold Springs Harbor, N.Y. 1989). One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used herein, the terms "nerve growth factor" and "NGF" are defined as all mammalian species of native sequence NGF, including human.

"NGF receptor" refers to a polypeptide that is bound by or activated by NGF. NGF receptors include the TrkA receptor and the p75 receptor of any mammalian species, including humans.

The term "native sequence" in connection with NGF or any other polypeptide refers to a polypeptide that has the same amino acid sequence as a corresponding polypeptide derived from nature, regardless of its mode of preparation. Such native sequence polypeptide can be isolated from nature or can be produced by recombinant and/or synthetic means or any combinations thereof. The term "native sequence" specifically encompasses naturally occurring truncated or secreted forms (e.g., an extracellular domain sequence), naturally occurring variant forms (e.g., alternatively spliced forms) and naturally-occurring allelic variants of the full length polypeptides.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Chothia et al., *J. Mol. Biol.* 186:651 [1985]; Novotny and Haber, *Proc. Natl. Acad. Sci. U.S.A.* 82:4592 [1985]; Chothia et al., *Nature* 342: 877-883 [1989]).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al. (1991) supra). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment that contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called κ and λ, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., $IgG_1$, $IgG_2$, $IgG_3$, $IgG_4$, $IgA_1$, and $IgA_2$. The heavy-chain constant domains that correspond to the different classes of immunoglobulins are called α, δ, εγ, and μ respectively. The subunit structures and three-dimensional configurations of different classes of immunoglobulins are well known.

The term "antibody" specifically covers monoclonal antibodies, including antibody fragment clones.

"Antibody fragments" comprise a portion of an intact antibody, generally the antigen binding or variable region of the intact antibody. Examples of antibody fragments include Fab, Fab', $F(ab')_2$, and Fv fragments; diabodies; single-chain antibody molecules, including single-chain Fv (scFv) molecules; and multispecific antibodies, such as bispecific antibodies, formed from antibody fragments.

The term "monoclonal antibody" as used herein refers to an antibody (or antibody fragment) obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. In addition to their specificity, the monoclonal antibodies are advantageous in that they are synthesized by the hybridoma culture, and are not contaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature,* 256:495 (1975), or may be made by recombinant DNA methods (see, e.g., U.S. Pat. No. 4,816,567). The "monoclonal antibodies" also include clones of antigen-recognition and binding-site containing antibody fragments (Fv clones) isolated from phage antibody libraries using the techniques described in Clackson et al., *Nature,* 352:624-628 (1991) and Marks et al., *J. Mol. Biol.,* 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567 to Cabilly et al.; Morrison et al., *Proc. Natl. Acad. Sci. USA*, 81:6851-6855 [1984]).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementarity-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., *Nature*, 321:522-525 (1986); Reichmann et al., *Nature*, 332:323-329 (1988); Presta, *Curr. Op. Struct. Biol.*, 2:593-596 (1992); and Clark, *Immunol. Today* 21: 397-402 (2000). The humanized antibody includes a Primatized™ antibody wherein the antigen-binding region of the antibody is derived from an antibody produced by immunizing macaque monkeys with the antigen of interest.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains, which enables the scFv to form the desired structure for antigen binding. For a review of scFv see Pluckthun, in *The Pharmacology of Monoclonal Antibodies*, vol. 113, Rosenburg and Moore eds., Springer-Verlag, New York, pp. 269-315 (1994), Dall'Acqua and Carter, *Curr. Opin. Struct. Biol.* 8: 443-450 (1998), and Hudson, *Curr. Opin. Immunol.* 11: 548-557 (1999).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 931/11161; and Hollinger et al., *Proc. Natl. Acad. Sci. USA*, 90:6444-6448 (1993).

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

By "neutralizing antibody" is meant an antibody molecule that is able to block or significantly reduce an effector function of a target antigen to which it binds. Accordingly, a "neutralizing" anti-NGF antibody is capable of blocking or significantly reducing an effector function, such as receptor binding and/or elicitation of a cellular response, of NGF. "Significant" reduction means at least about 60%, preferably at least about 70%, more preferably at least about 75%, even more preferably at least about 80%; still more preferably at least about 85%, most preferably at least about 90% reduction of an effector function of the target antigen (e.g. NGF).

An antibody is capable of "inhibiting the binding" of a ligand to a receptor when it is capable of producing an objectively measurable decrease in the ability of the ligand to bind the receptor.

The term "epitope" is used to refer to binding sites for (monoclonal or polyclonal) antibodies on protein antigens.

Antibodies which bind to a particular epitope can be identified by "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. Competition assays are discussed below. According to the gene fragment expression assays, the open reading frame encoding the protein is fragmented either randomly or by specific genetic constructions and the reactivity of the expressed fragments of the protein with the antibody to be tested is determined. The gene fragments may, for example, be produced by PCR and then transcribed and translated into protein in vitro, in the presence of radioactive amino acids. The binding of the antibody to the radioactively labeled protein fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. The latter approach is suitable to define linear epitopes of about 5 to 15 amino acids.

An antibody binds "essentially the same epitope" as a reference antibody, when the two antibodies recognize identical or sterically overlapping epitopes. The most widely used and rapid methods for determining whether two epitopes bind to identical or sterically overlapping epitopes are competition assays, which can be configured in all number of different formats, using either labeled antigen or labeled antibody. Usually, the antigen is immobilized on a 96-well plate, and the ability of unlabeled antibodies to block the binding of labeled antibodies is measured using radioactive or enzyme labels.

The term amino acid or amino acid residue, as used herein, refers to naturally occurring L amino acids or to D amino acids as described further below with respect to variants. The commonly used one- and three-letter abbreviations for amino acids are used herein (Bruce Alberts et al., Molecular Biology of the Cell, Garland Publishing, Inc., New York (3d ed. 1994)).

"Variants" are antibodies that differ in some respect from native antibodies while retaining the same biological activity. Variants may have an amino acid sequence that differs from the sequence of the native antibody as a result of an insertion, deletion, modification and/or substitution of one or more amino acid residues within the native sequence. Variants may have a different glycosylation pattern from native antibodies. Further, variants may be native antibodies that have been covalently modified.

A "disorder" is any condition that would benefit from treatment according to the present invention. "Disorder" and "condition" are used interchangeably herein and include chronic and acute disorders or diseases, including those pathological conditions which predispose the mammal to the disorder in question. Non-limiting examples of disorders to be treated herein include lupus erythematosus, contact dermititis, eczema, shingles, postherpetic neuralgia, hyperalgesia, chronic pain, irritable bowel disease, Crohn's disease, colitis, bladder cystitis, multiple sclerosis, asthma, psoriasis, and arthritis, including chronic arthritis and rheumatoid arthritis. A preferred disorder to be treated in accordance with the present invention is an inflammatory condition, such as asthma, multiple sclerosis, arthritis, lupus erythematosus and psoriasis.

An "inflammatory condition" is a condition characterized by one or more of pain, heat, redness, swelling and loss of function, and is associated with tissue injury, infection, irritation or damage.

The term "disease state" refers to a physiological state of a cell or of a whole mammal in which an interruption, cessation, or disorder of cellular or body functions systems, or organs has occurred.

The term "effective amount" or "therapeutically effective amount" refers to an amount of a drug effective to treat and/or prevent a disease, disorder or unwanted physiological condition in a mammal. In the present invention, an "effective amount" of an anti-NGF antibody may prevent, reduce, slow down or delay the onset of a disorder such as lupus, multiple sclerosis, asthma, psoriasis or arthritis; reduce, prevent or inhibit (i.e., slow to some extent and preferably stop) the development of a disorder such as lupus, multiple sclerosis, asthma, psoriasis or arthritis; and/or relieve, to some extent, one or more of the symptoms associated with such a disorder.

In the methods of the present invention, the term "control" and grammatical variants thereof, are used to refer to the prevention, partial or complete inhibition, reduction, delay or slowing down of an unwanted event, e.g. physiological condition, such as the inflammatory response associated with a disorder such as asthma.

"Treatment" or "treat" refers to both therapeutic treatment and prophylactic or preventative measures. Those in need of treatment include those already with the disorder as well as those prone to have the disorder or those in which the disorder is to be prevented. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

A "significant adverse effect" on the immune system is an effect that compromises the immune system and/or inhibits a normal immune response to antigen challenge. An example of a significant adverse effect on the immune system would be a reduced humoral immune response.

"Pharmaceutically acceptable" carriers, excipients, or stabilizers are ones which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN, polyethylene glycol (PEG), and PLURONICS.

A "liposome" is a small vesicle composed of various types of lipids, phospholipids and/or surfactant which is useful for delivery of a drug (such as the anti-NGF antibodies disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

"Mammal" for purposes of treatment refers to any animal classified as a mammal, including humans, domestic and farm animals, and zoo, sports, or pet animals, such as dogs, horses, cats, cows, etc. Preferably, the mammal is human.

B. Methods for Carrying Out the Invention

As described in more detail below, administration of anti-NGF monoclonal antibody 911 in a mouse model of asthma reduced measures of airway hyperreactivity and inflammation but did not decrease the humoral immune response to inhaled antigen as measured by total serum immunoglobulin levels and serum level of IgE.

Anti-NGF antibodies are known in the art. The anti-NGF antibodies useful in the present invention include polyclonal antibodies, monoclonal antibodies, chimeric antibodies, humanized antibodies, human antibodies, bispecific antibodies, heteroconjugate antibodies, and antibody fragments, as well as modified antibodies, including glycosylation variants of antibodies, amino acid sequence variants of antibodies and covalently modified antibodies. The antibodies can be made by any method known in the art.

Thus, monoclonal antibodies may be made using the hybridoma method first described by Kohler et al., *Nature*, 256:495 (1975), or by recombinant DNA methods (U.S. Pat. No. 4,816,567).

Briefly, in the hybridoma method, a mouse or other appropriate host animal, such as a hamster or macaque monkey, is immunized to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103, [Academic Press, 1986]). The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. Preferred myeloma cell lines are murine myeloma lines, such as those derived from MOP-21 and MC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63, Marcel Dekker, Inc., New York, [1987]). Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA). The binding affinity of the monoclonal antibody can, for example, be determined by the Scatchard analysis of Munson et al., *Anal. Biochem.*, 107:220 (1980). After hybridoma cells are identified that produce antibodies of the desired specificity, affinity, and/or activity, the cells may be subcloned by limiting dilution procedures and grown by standard methods (Goding, *Monoclonal Antibodies: Principles and Practice*, pp. 59-103 (Academic Press, 1986)). The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Recombinant production of the antibodies requires the isolation of DNA encoding the antibody or antibody chains. DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison, et al., *Proc. Nat. Acad. Sci.* 81, 6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-NGF monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for a native NGF polypeptide and another antigen-combining site having specificity for a different target, such as a high-affinity IgE receptor, or a TNF receptor. Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

Non-human, such as murine antibodies can be humanized. Generally, a humanized antibody has one or more amino acid residues introduced into it from a non-human source. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239: 1534-1536 (1988)), by substituting rodent CDRs or CDR sequences for the corresponding sequences of a human antibody.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details, see U.S. Pat. No. 5,821,337.

The invention also includes human anti-NGF antibodies. As noted before, such human antibodies can be made by the hybridoma method, using human myeloma or mouse-human heteromyeloma cell lines for the production of human monoclonal antibodies (see, e.g. Kozbor, *J. Immunol.* 133, 3001 (1984), and Brodeur, et al., *Monoclonal Antibody Production Techniques and Applications*, pp. 51-63 (Marcel Dekker, Inc., New York, (1987)). Furthermore, it is possible to produce transgenic animals (e.g. mice) that are capable, upon immunization, of producing a repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al.,

*Proc. Natl. Acad. Sci. USA* 90, 2551-255 (1993); Jakobovits et al., *Nature* 362, 255-258 (1993). For an improved version of this technology, see also Mendez et al. (*Nature Genetics* 15: 146-156 (1997)).

Alternatively, the phage display technology (McCafferty at al., *Nature* 348, 552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g. Johnson, Kevin S. and Chiswell, David J., *Current Opinion in Structural Biology* 3, 564-571 (1993). Several sources of V-gene segments can be used for phage display. Clackson at al., *Nature* 352, 624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222, 581-597 (1991), or Griffiths at al., *EMBO J.* 12, 725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., *Bio/Technol.* 10, 779-783 [1992]). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the nM range. A strategy for making very large phage antibody repertoires (also known as "the mother-of-all libraries") has been described by Waterhouse et al., *Nucl. Acids Res.* 21, 2265-2266 (1993), and the isolation of a high affinity human antibody directly from such large phage library is reported by Griffiths et al., *EMBO J.* 13: 3245-3260 (1994).

Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable domains capable of restoring a functional antigen-binding site, i.e. the epitope governs (imprints) the choice of partner. When the process is repeated in order to replace the remaining rodent V domain, a human antibody is obtained (see PCT patent application WO 93106213, published 1 Apr. 1993). Unlike traditional humanization of rodent antibodies by CDR grafting, this technique provides completely human antibodies, which have no framework or CDR residues of rodent origin.

The present invention specifically includes bispecific antibodies. Traditionally, the recombinant production of bispecific antibodies is based on the co-expression of two immunoglobulin heavy chain-light chain pairs, where the two heavy chains have different specificities (Millstein and Cuello, *Nature* 305, 537-539 (1983)). According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. For further details of generating bispecific antibodies see, for example, Suresh at al., *Methods in Enzymology* 121, 210 (1986).

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Antibody fragments have been traditionally derived via proteolytic digestion of intact antibodies (see, e.g., Morimoto et al., *J. Biochem. Biophys. Methods* 24:107-117 (1992) and Brennan et al., *Science* 229:81 (1985)). However, these fragments can now be produced directly by recombinant host cells. For example, Fab'-SH fragments can be directly recovered from *E. coli* and chemically coupled to form $F(ab')_2$ fragments (Carter et al., *Bio/Technology* 10:163-167 (1992)). In another embodiment, the $F(ab')_2$ is formed using the leucine zipper GCN4 to promote assembly of the $F(ab')_2$ molecule. According to another approach, Fv, Fab or $F(ab')_2$ fragments can be isolated directly from recombinant host cell culture. Other techniques for the production of antibody fragments will be apparent to the skilled practitioner.

For use in certain embodiments of the invention, it may be desirable to modify the antibody fragment in order to increase its serum half-life. This may be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis). See WO 96132478 published Oct. 17, 1996.

The salvage receptor binding epitope generally constitutes a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or $V_H$ region, or more than one such region, of the antibody. Alternatively, the epitope is taken from the CH2 domain of the Fc region and transferred to the $C_L$ region or $V_L$ region, or both, of the antibody fragment.

Amino acid sequence variants, including substitution, insertion and/or deletion variants, of the anti-NGF antibodies specifically disclosed are prepared by introducing appropriate nucleotide changes into the encoding DNA, or by peptide synthesis. Methods for making such variants are Well known in the art, and include, for example, "alanine scanning mutagenesis," as described by Cunningham and Wells *Science*, 244:1081-1085 (1989). A particular type of amino acid variant of an antibody alters the original glycosylation pattern of the antibody. By altering is meant deleting one or more carbohydrate moieties found in the antibody, and/or adding one or more glycosylation sites that are not present in the antibody.

Screening for Antibodies with the Desired Properties

Antibodies useful in the present invention are those that neutralize the activity of NGF. Thus, for example, the neutralizing anti-NGF antibodies of the present invention can be identified by incubating a candidate antibody with NGF and monitoring binding and neutralization of a biological activity of NGF. The binding assay may be performed with purified NGF polypeptide(s), or with cells naturally expressing, or transfected to express, NGF polypeptide(s). In one embodiment, the binding assay is a competitive binding assay, where the ability of a candidate antibody to compete with a known anti-NGF antibody for NGF binding is evaluated. The assay may be performed in various formats, including the ELISA format.

The ability of a candidate antibody to neutralize a biological activity of NGF can, for example, be carried out by monitoring the ability of the candidate antibody to inhibit NGF mediated survival in the embryonic rat dorsal root ganglia survival bioassay as described in Hongo et al. (Hybridoma 19:215-227 (2000)).

To screen for antibodies which bind to an epitope on NGF bound by an antibody of interest, a routine cross-blocking assay such as that described in *Antibodies, A Laboratory Manual*, Cold Spring Harbor Laboratory, Ed Harlow and David Lane (1988), can be performed. Alternatively, or additionally, epitope mapping can be performed by methods known in the art. For example, the NGF epitope bound by a monoclonal antibody of the present invention can be determined by competitive binding analysis as described in Fendly et al. *Cancer Research* 50:1550-1558 (1990). Cross-blocking studies can be done by direct fluorescence on intact cells using the PANDEX™ Screen Machine to quantitate fluorescence. In this method the monoclonal antibody is conjugated with fluorescein isothiocyanate (FITC), using established procedures (Wofsy et al. *Selected Methods in Cellular Immunology*, p. 287, Mishel and Schiigi (eds.) San Francisco: W.J. Freeman Co. (1980)). NGF expressing cells in suspension and purified monoclonal antibodies are added to the PANDEX™ plate wells and incubated, and fluorescence is quantitated by the PANDEX™. Monoclonal antibodies are considered to share an epitope if each blocks binding of the other by 50% or greater in comparison to an irrelevant monoclonal antibody control.

Anti-NGF antibodies useful in the present invention can also be identified using combinatorial libraries to screen for synthetic antibody clones with the desired activity or activities. Such methods are well known in the art. Briefly, synthetic antibody clones are selected by screening phage libraries containing phage that display various fragments (e.g. Fab, F(ab')$_2$, etc. . . . ) of antibody variable region (Fv) fused to phage coat proteins. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen and can be further enriched by additional cycles of antigen adsorption/elution. Suitable anti-NGF antibodies for use in the present invention can be obtained by designing a suitable antigen screening procedure to select for the phage clone of interest, followed by construction of a full length anti-NGF antibody clone by using the Fv sequences from the phage clone of interest and a suitable constant region (Fc) sequence.

The results obtained in the cell-based biological assays can be followed by testing in animal, e.g. murine, models and human clinical trials. If desired, murine monoclonal antibodies identified as having the desired properties can be converted into chimeric antibodies, or humanized by techniques well known in the art, including the "gene conversion mutagenesis" strategy, as described in U.S. Pat. No. 5,821,337.

C. Pharmaceutical Formulations

Therapeutic formulations of the antibody used in accordance with the present invention are prepared for storage by mixing an antibody having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN, PLURONICS or polyethylene glycol (PEG).

The neutralizing anti-NGF antibodies useful in the methods of the present invention may also be formulated as immunoliposomes. Liposomes containing the antibody are prepared by methods known in the art, such as described in Epstein et al., *Proc. Natl. Acad. Sci. USA* 82:3688 (1985); Hwang et al., *Proc. Natl Acad. Sci. USA* 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257: 286-288 (1982) via a disulfide interchange reaction. A chemotherapeutic agent (such as Doxorubicin) is optionally contained within the liposome. See Gabizon et al., *J. National Cancer Inst.* 81(19):1484 (1989).

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT (injectable microspheres composed of lactic acid-glycolic acid copolymer and leuprolide acetate), and poly-D-(−)-3-hydroxybutyric acid.

The formulation herein may also contain more than one active compound as necessary for the particular indication being treated, preferably compounds with complementary activities that do not adversely affect each other. For example, it may be desirable to further provide antibodies that bind to a different epitope of NGF or to an NGF receptor in the one formulation. Alternatively, or additionally, the composition may further comprise another biologically active compound, such as an anti-inflammatory agent. Such molecules are suitably present in combination in amounts that are effective for the purpose intended.

The formulations to be used for in vivo administration must be sterile. This is readily accomplished by, for example, filtration through sterile filtration membranes.

Therapeutic anti-NGF antibody compositions are generally placed into a container having a sterile access port, for example, an intravenous solution bag or vial having a stopper pierceable by a hypodermic injection needle.

D. Treatment with Anti-NGF Antibodies

It is contemplated that, according to the present invention, the anti-NGF antibodies may be used to treat various diseases or disorders. Exemplary conditions or disorders include asthma, psoriasis and arthritis. The anti-NGF antibodies may be used to prevent the onset of the active disease state, to treat symptoms that are currently being experienced and to treat the underlying disease itself.

Despite advances in understanding the cellular and molecular mechanisms that control allergic responses and improved therapies, the incidence of allergic diseases, especially asthma, has increased dramatically in recent years (Beasley et al., *J. Allergy Clin. Immunol.* 105:466-472 (2000); Peat and Li, *J. Allergy Clin. Immunol.* 103:1-10 (1999)). Allergic diseases can be treated, for example, by allergen-based vaccination, in which increasing doses of allergen are given by injection over years. Mild asthma can usually be controlled in most patients by relatively low doses of inhaled corticosteroids, while moderate asthma is usually managed by the additional administration of inhaled long-acting β-antagonists or leukotriene inhibitors. However, the treatment of severe asthma is still a serious medical problem. Although an anti-IgE antibody currently awaiting FDA approval (rhuMAb-E25, Xolair™, developed in collaboration of Genentech, Inc., Tanox, Inc. and Novartis Pharmaceuticals Corporation) shows promising results for early intervention in the treatment of conditions that lead to symptoms of allergic asthma and seasonal allergic rhinitis, there is need for the development of additional therapeutic strategies and agents to control allergic diseases, such as asthma.

The anti-NGF antibodies of the present invention can be used for the treatment of asthma and other disorders associated with airway hyperreactivity, typically characterized by episodes of coughs, wheezing, chest tightness, and/or breathing problems.

The anti-NGF antibodies of the present invention are also useful in the management of other inflammatory conditions, such as multiple sclerosis, colitis, inflammatory bowel disease, bladder cystitis, eczema, contact dermititis, arthritis, including chronic arthritis and rheumatoid arthritis, Crohn's disease, and psoriasis.

In addition, anti-NGF antibodies are also useful in treating other diseases that may be associated with increased levels of NGF including, for example, lupus erythematosus, shingles, postherpetic neuralgia, hyperalgesia, and chronic pain.

The anti-NGF antibodies are administered to a mammal, preferably to a human patient, in accord with known methods, such as intravenous administration, e.g., as a bolus or by continuous infusion over a period of time, by intramuscular, intraperitoneal, intracerebrospinal, subcutaneous, intra-articular, intrasynovial, intrathecal, oral, or topical routes. Anti-NGF antibody can also be administered by inhalation. Commercially available nebulizers for liquid formulations, including jet nebulizers and ultrasonic nebulizers are useful for administration. Liquid formulations can be directly nebulized and lyophilized powder can be nebulized after reconstitution. Alternatively, anti-NGF antibody can be aerosolized using a fluorocarbon formulation and a metered dose inhaler, or inhaled as a lyophilized and milled powder. For the treatment of asthma and other conditions characterized by airway hyperreactivity, a preferred route of administration is by inhalation.

Other therapeutic regimens may be combined with the administration of the anti-NGF antibody. The combined administration includes co-administration, using separate formulations or a single pharmaceutical formulation, and consecutive administration, in any order, wherein preferably there is a time period while both (or all) active agents simultaneously exert their biological activities. For the treatment of asthma, it might be particularly advantageous to use the antibodies herein in combination with anti-IgE antibodies, in particular rhuMAb-E25 (Xolair™), or with second-generation antibody molecule rhuMAb-E26 (Genentech, Inc.). The rhuMAb-E25 antibody is a recombinant humanized anti-IgE monoclonal antibody that was developed to interfere early in the allergic process. Combination use also includes the possibility of administering the two antibodies in a single pharmaceutical formulation, or using a bispecific antibody, with anti-NGF and anti-IgE specificities. In another preferred embodiment, the anti-NGF antibodies herein are administered in combination with inhaled corticosteroids, such as beclomethasone diproprionate (BDP) treatment. For the treatment of rheumatoid arthritis or Crohn's disease, the antibodies of the present invention can be administered in combination with other treatment regimens known for the treatment of these conditions. For example, the anti-NGF antibodies herein can be administered in combination with Remicade® (Infliximab, Centocor), or Enbrel® (Etanercept, Wyeth-Ayerst). The present invention also includes bispecific antibodies targeting these diseases. For example, a bispecific antibody could include an anti-TNF specificity combined with the NGF-binding ability of the antibodies herein.

Suitable dosages for any of the above co-administered agents are those presently used and may be lowered due to the combined action (synergy) of the agent and anti-NGF antibody.

For the prevention or treatment of disease, the appropriate dosage of anti-NGF antibody will depend on the anti-NGF antibody employed, the type of disease to be treated, the severity and course of the disease, whether the antibody is administered for preventive or therapeutic purposes, previous therapy, the patient's clinical history and response to the antibody, and the discretion of the attending physician. Typically the clinician will administer the anti-NGF antibody until a dosage is reached that achieves the desired result.

The anti-NGF antibody is suitably administered to the patient at one time or over a series of treatments. Depending on the type and severity of the disease, about 2 mg/kg of antibody is an initial candidate dosage for administration to the patient, whether, for example, by one or more separate administrations, or by continuous or repeated dosing. A typical daily dosage might range from about 1 g/kg to 100 mg/kg or more, depending on the factors mentioned above. For repeated administrations over several days or longer, depending on the condition, the treatment is sustained until a desired suppression of disease symptoms occurs. A preferred dosing regimen comprises administering an initial dose of about 2 mg/kg, followed by a weekly maintenance dose of about 1 mg/kg of the anti-NGF antibody. However, other dosage regimens may be useful, depending on the pattern of pharmacokinetic decay that the practitioner wishes to achieve. The progress of this therapy is easily monitored by conventional techniques and assays.

E. Articles of Manufacture

In another embodiment of the invention, an article of manufacture containing materials useful for the treatment of the disorders described above is provided. The article of manufacture comprises a container and a label or package insert(s) on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is an anti-NGF antibody. The container may further comprise a second pharmaceutically active agent. Preferably the second agent is suitable for the treatment of an inflammatory disease such as asthma, multiple sclerosis, arthritis, lupus erythematosus and psoriasis.

The label or package insert indicates that the composition is used for treating the condition of choice, such as an inflammatory condition. In one embodiment, the label or package inserts indicates that the composition comprising the antibody that binds NGF can be used to treat an inflammatory condition selected from the group consisting of asthma, multiple sclerosis, arthritis, lupus erythematosus and psoriasis. In addition, the label or package insert may indicate that the patient to be treated is one having asthma, psoriasis, arthritis or another disease or disorder. Moreover, the article of manufacture may comprise (a) a first container with a composition contained therein, wherein the composition comprises a first antibody which binds NGF and inhibits its biological activity; and (b) a second container with a composition contained therein, wherein the composition comprises a second antibody which binds an NGF receptor and blocks ligand activation. The article of manufacture in this embodiment of the invention may further comprise a package insert indicating that the first and second compositions can be used to treat asthma, psoriasis, arthritis or another disease or disorder. Alternatively, or additionally, the article of manufacture may further comprise a second (or third) container comprising a pharmaceutically acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

Further details of the invention are illustrated in the following non-limiting examples.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Production and Characterization of Anti-NGF Monoclonal Antibodies

A. Production of Anti-NGF Monoclonal Antibodies

This example illustrates preparation of monoclonal antibodies that can specifically bind human NGF (hNGF). Techniques for producing monoclonal antibodies are well known in the art and are described, for instance, in Kohler and Milstein, *Nature* 256:495-497 (1975). The experiments described in Examples 1 and 2 are further described in Hongo et al., *Hybridoma* 19:215.227.

A panel of 23 murine monoclonal antibodies to hNGF was developed by a method analogous to that described in Hongo et al., *Hybridoma* 14:253-260. Briefly, Balb/c mice (Charles River Laboratories, Wilmington, Del.) were immunized with human NGF in Ribi adjuvant (Ribi Immunochem Research, Inc., Hamilton, Md.). Splenocytes from the mouse demonstrating the highest titer of antibody to immobilized NGF were fused with mouse myeloma cells (X63.Ag8.653; American Type Culture Collection, Rockville, Md.). After 10-14 days, supernatants were harvested and screened for antibody production by enzyme-linked immunosorbent assay (ELISA). Clones showing the highest immunoreactivity after the second round of cloning were injected into Pristane-primed mice (Hoogenraad et al., *J. Immunol. Methods* 6:317-320 (1983)) for in vivo production of MAb. The ascites fluids were pooled and purified by affinity chromatography (Pharmacia fast protein liquid chromatography; Pharmacia, Uppsala, Sweden) using an established procedure (Moks et al.,

*Eur. J. Biochem.* 85:1205-1210 (1986)) on staphylococcal protein A (Pharmacia). The purified antibody preparations were sterile filtered and stored at 4° C. in phosphate-buffered saline (PBS).

B. Epitope Mapping Using Domain Swap Mutants

Epitope specificity of anti-NGF MAbs was initially determined by evaluating binding of the MAbs to chimeric NGF/neurotrophin-3 (NT-3) proteins generated through homolog-scanning mutagenesis. The use of such domain-swap mutants has a distinct advantage over deletion mutants. The deletion of a domain might disrupt the secondary structure of the protein whereas substitution of a domain with a corresponding domain, of similar size and substantially similar amino acid sequence, from a related protein in domain-swap mutants is likely to retain the secondary structure.

Eight hNGF/hNT-3 chimeric mutants, containing three to seven residue substitutions of the human NT-3 (hNT-3) sequence into the corresponding variable regions of hNGF (FIG. 1) were produced by oligonucleotide-directed mutagenesis. The chimeric mutants were transiently expressed in human 293 cells, and the binding of anti-hNGF MAbs to mutant NGF was evaluated by enzyme-linked immunosorbent assay (ELISA), as described below, using the purified MAb as the capture antibody and an HRP-conjugated affinity-purified rabbit anti-hNGF polyclonal antibody for detection. Binding of anti-hNGF MAbs to each NGF mutant was determined from two to four independent quantitative ELISA runs and was compared to binding to wild-type NGF.

Briefly, microtiter plates (Nunc Maxisorb, VWR Scientific, San Francisco, Calif.) were coated with 100 L per well of 1 g/mL goat anti-mouse IgG (Boehringer-Mannheim, Indianapolis, Ind.) overnight at 4° C., washed, and the excess binding sites were blocked with PBS containing 0.05% Tween 20 with 0.5% bovine serum albumin (BSA, Intergen, San Diego, Calif.; PBS/BSA/T20). MAbs (diluted to 1 g/mL in PBS/BSA/T20) were added to the appropriate wells and incubated for 1-2 hours at ambient temperature. The plates were washed, and 100 L of wild-type or mutant hNGF (diluted in PBS/BSA/T20 to 60 ng/mL 7.8 ng/mL) were added, incubated for 1-2 hours at ambient temperature, and again washed. Purified rabbit anti-hNGF polyclonal antibody conjugated to horseradish peroxidase (HRP; 1:10,000 in PBS/BSA/T20) was added 100 L/well) and incubated for 1 hour. The plates were developed and read on dual wavelength. Binding of the MAbs to the hNGF mutants was compared to wild-type hNGF binding (set at 100%) analyzed under the same conditions.

Figure 3A:
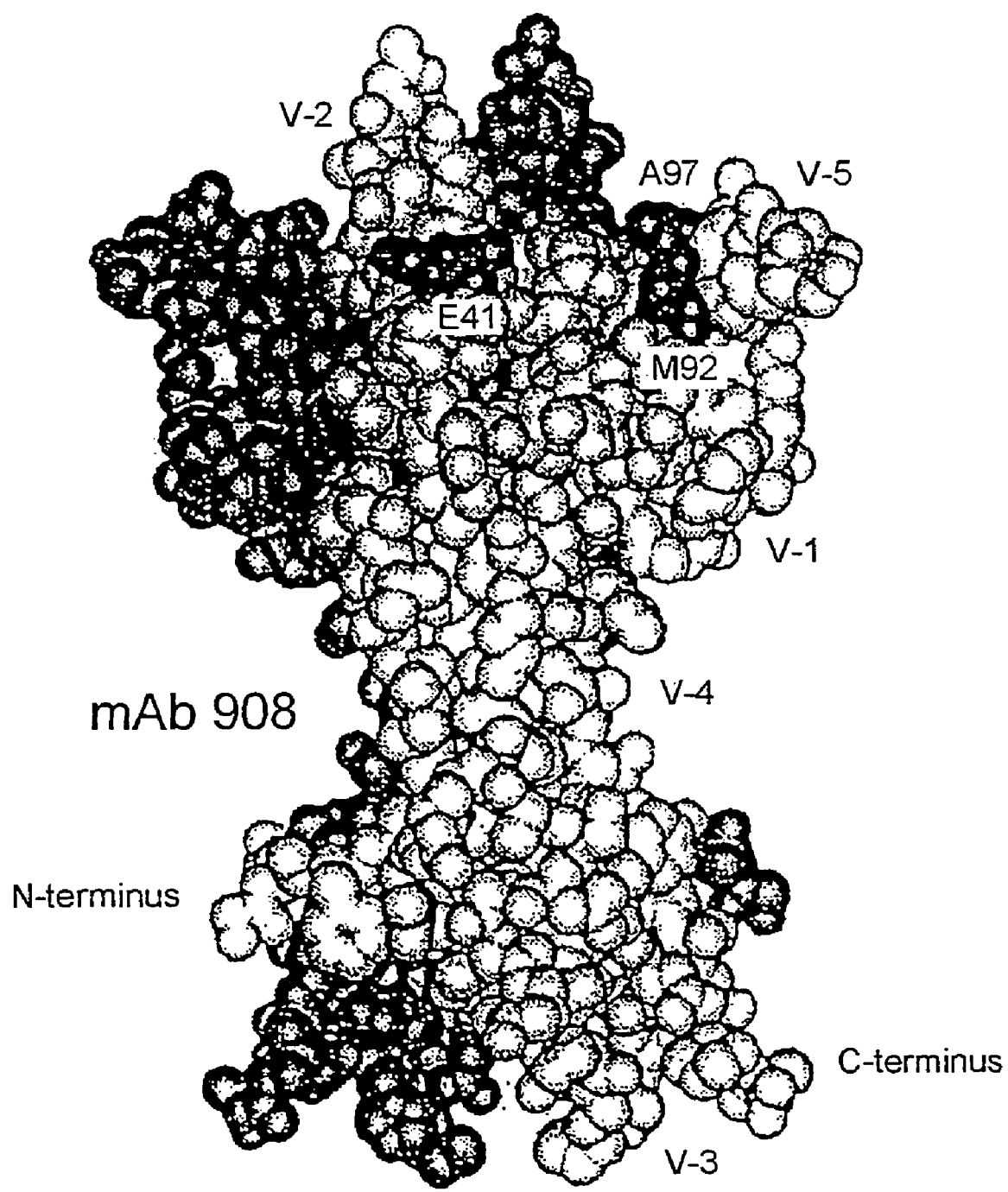
Figure 3B:
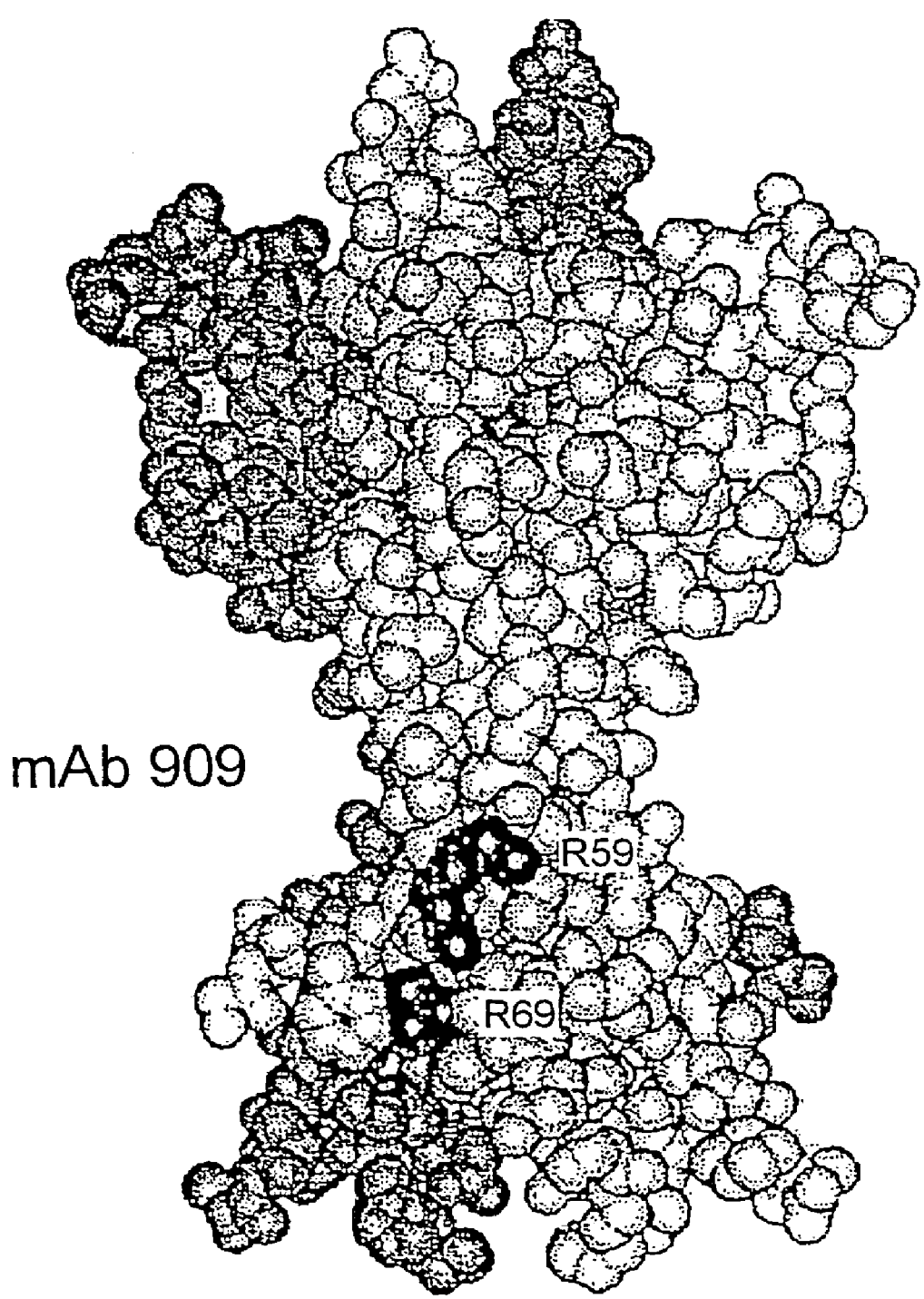
Figure 3C:
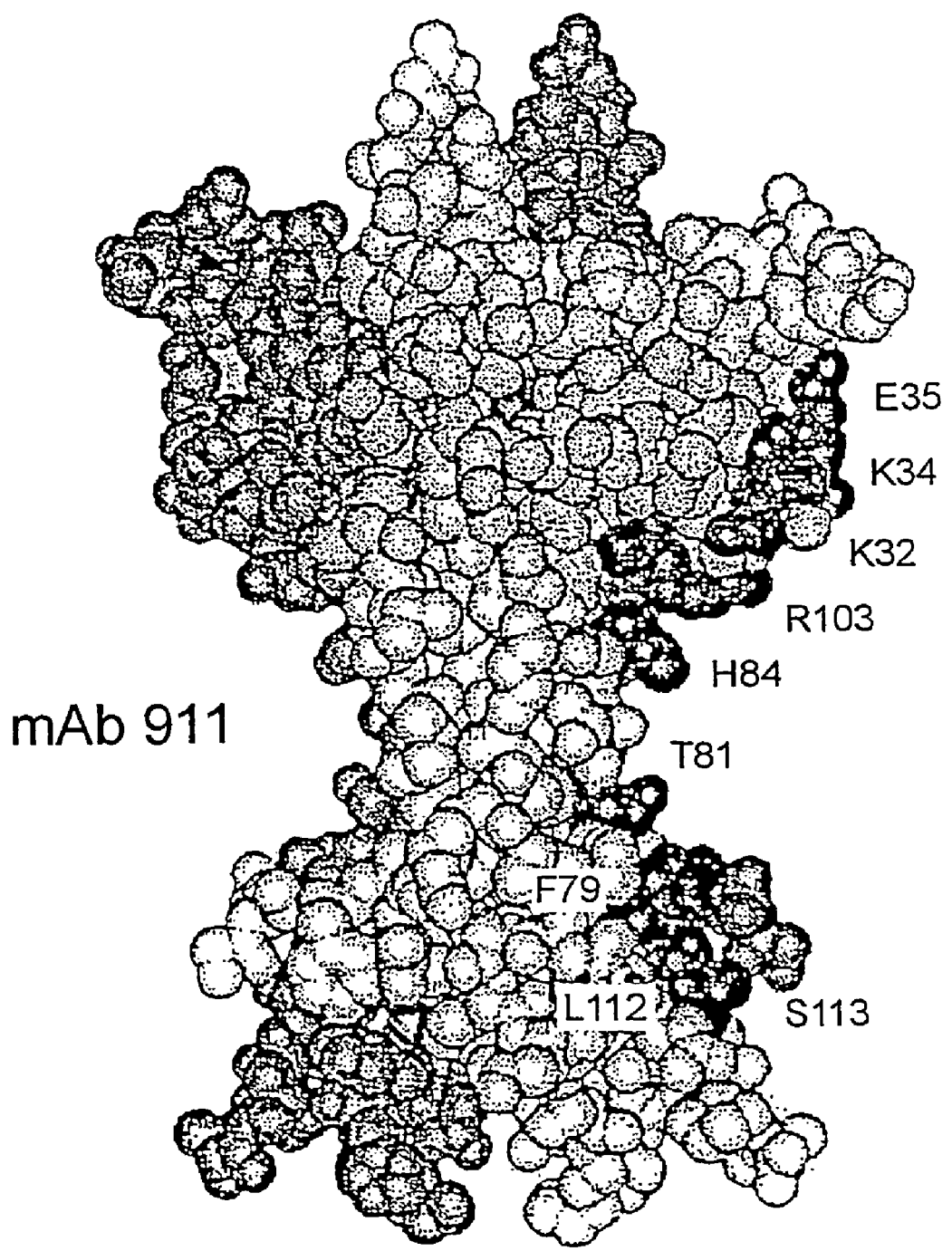

Six human anti-NGF monoclonal antibodies (MAb 908, 909, 911, 912, 938 and 14.14) that demonstrated high affinities for hNGF ($EC_{50}$=0.18 nM for MAb 908, 0.18 nM for MAb 909, 0.37 nM for MAb 911, 0.18 for MAb 912, 0.74 for MAb 938 and 0.59 for MAb 14.14) and a greater than 60-90% reduction in binding to the various chimeric mutants (FIG. 1) were selected for further analysis. As shown in FIG. 1, three of the MAbs (908, 909 and 14.14) displayed clear regional binding specificity, characterized by loss of 60-95% maximal binding to a single variable region (FIG. 1). Less dramatic effects of variable region mutants were observed for MAbs 911, 912 and 938, with multiple NGF variable regions contributing to the binding epitopes of these antibodies. However, the variable regions that comprise these epitopes are close together within the three-dimensional structure (FIG. 3A).

C. Epitope Mapping Using Site-Directed Mutagenesis

To further define the epitope specificity of each of the six anti-NGF MAbs selected, NGF mutants representing single, double, or triple amino acid point mutations were generated, expressed and characterized, with a particular focus on residues within regions previously reported to play a role in TrkA and p75 binding and biological function (Shih et al., *J. Biol. Chem.,* 269(44):27679-27686 (1994)). The effects of the mutations on anti-NGF MAb binding were characterized by ELISA as described above. Average $EC_{50}$ values for binding of the anti-NGF MAbs to each mutant were calculated from ELISA binding curves and compared to $EC_{50}$ values obtained for wild-type NGF binding (FIGS. 2A-F).

With all six MAbs, the binding specificity of the hNGF point mutants generally correlated with the regions previously identified by loss of binding to specific NGF chimeric mutants. However, the effects of NGF point mutations on the binding of MAbs 911 and 938 were less prominent relative to the effects observed on the other MAbs (FIGS. 2A-F). The regional specificity of the mutational effects correlated with residues within or near variable regions swapped in the NGF chimeric mutants, and which resulted in the loss of more than 50-60% of the maximal binding of MAbs 911 or 938. For MAb 911, these mutations included K32A+K34A+E35A, Y79A+T81K, H84A+K88A, and R103A. Additional loss of binding was observed with the nearby mutations E11A, Y52A and L112A+S113A (FIG. 2C). This indicates that the epitope for MAb 911 spans four of the seven hNGF variable regions (FIG. 3C).

D. Structural Dependency of Epitopes for Binding by MAbs

To determine whether binding of anti-NGF MAbs to hNGF depends upon the structural conformation of epitopes on hNGF, binding of the anti-NGF MAbs to non-reduced and reduced forms of hNGF was evaluated. hNGF, either untreated or reduced by treatment with mercaptoethanol, was subjected to gel electrophoresis and transferred to nitrocellulose blots for immunoblotting. For detection of hNGF, the nitrocellulose blots were washed, incubated with primary and secondary antibodies, exposed to luminol substrate (Amersham International, Amersham, U.K.) for 1 minute at ambient temperature with agitation, and exposed to x-ray film (Eastman Kodak, Rochester, N.Y.) for 10-45 seconds. In FIG. 4 it can be seen that several monoclonal anti-NGF antibodies exhibit minimal binding to reduced forms of hNGF. These included MAb 938, 908, 911 and 912, indicating that epitopes on hNGF to which they bind are structurally affected by charge alteration and reduction.

E. Molecular Modeling of Epitopes on Anti-NGF Monoclonal Antibodies

Molecular modeling representations of the identified anti-NGF MAb epitopes (FIGS. 3A-F) were produced using the program MidasPlus (University of California at San Francisco, San Francisco, Calif.) and were based on coordinates for the three-dimensional structure of murine NGF as previously described (McDonald et al., *Nature,* 354:411-414 (1991)).

A summary of the MAb epitope mapping results is presented in FIG. 5.

Example 2

Determination of Neutralizing Activity of Anti-NGF Monoclonal Antibodies

The observation that some epitopes mapped in regions previously shown to be significant in the interaction of NGF with TrkA and/or p75 suggested that the corresponding MAbs might also block one or both of these interactions.

A. $^{125}$I-hNGF Binding Assay.

To evaluate the possibility that one or more of the anti-NGF MAbs might block NGF binding to TrkA and/or p75, the binding of $^{125}$I-hNGF to the TrkA-IgG receptor immunoadhesin was measured in the presence of anti-NGF monoclonal antibodies.

Briefly, $^{125}$I-hNGF was prepared using a modification of the soluble lactoperoxidase method originally described by Marchalonis (Marchalonis, *Biochem J.*, 113:299-305 (1969)). The final reaction mixture was fractionated over a pD-10 Sephadex G-25 size exclusion column (Pharmacia, Uppsala, Sweden) and stored at 4° C. Microtiter plates (Nunc, Maxisorb) were coated overnight at 4° C. with purified rabbit anti-human IgG-Fc specific polyclonal antibody (diluted to 2 g/ml in carbonate buffer), washed with PBS, and blocked with 150 L of PBS/0.5% BSA (PBS/BSA). Human TrkA-IgG or p75-IgG immunoadhesins (kindly provided by Robert Pitti) (20 ng/mL) in PBS/BSA were added (100 L) and incubated at ambient temperature for 1 hour. hNGF diluted in PBS/BSA (150 pM final) was then added (100 L) and incubated for 1 hour at ambient temperature. hNGF (150 pM final) preincubated overnight at 4° C. with anti-NGF monoclonal antibodies (667 nM 0.58 nM) or an irrelevant monoclonal antibody not directed to NGF was added in parallel and incubated as described. The plates were washed with PBS containing 0.05% T20, and individual wells were counted for 1 minute on a gamma counter (Packard Cobra Model 5010, Downers Grove, Ill.).

Figure 6:
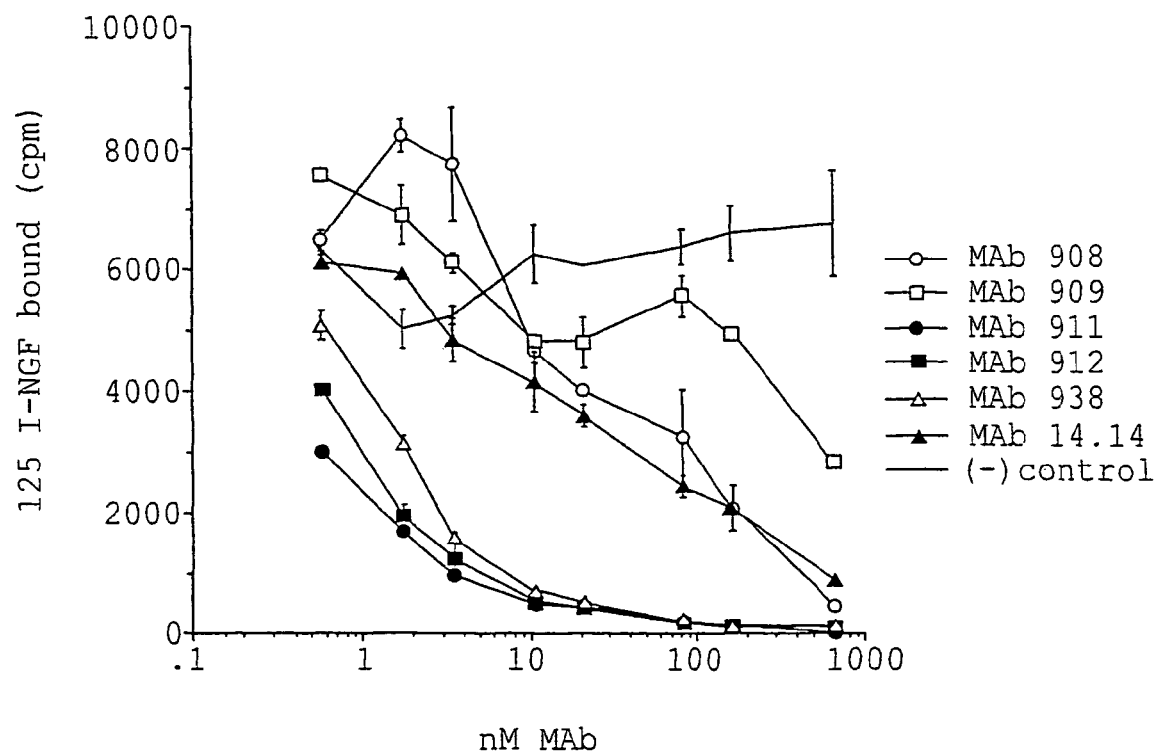

As can be seen FIG. 6, the anti-NGF monoclonal antibodies inhibited binding of hNGF to the TrkA-IgG receptor immunoadhesin as measured by the level of $^{125}$I-labeled hNGF bound to TrkA-IgG. All of the MAbs showed blocking ability at the highest concentration assayed (667 nM) but clearly showed different blocking capacity at lower concentrations. MAbs 911, 912 and 938 exhibited the same blocking potency ($IC_{50}$~0.5-2 nM), with 80-90% inhibition seen at 10 nM MAb or greater.

Figure 7:
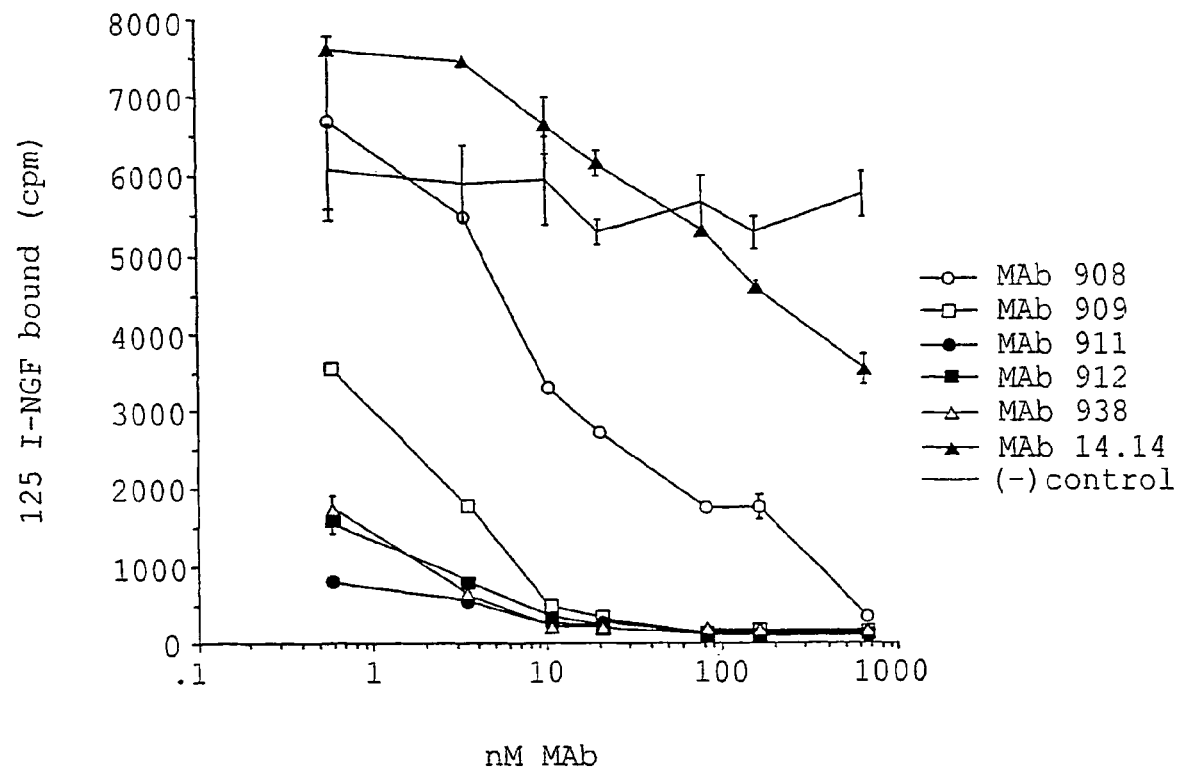

The ability of the MAbs to inhibit the binding of hNGF to the low affinity p75 receptor was evaluated using p75-IgG in the binding assay described above. As shown in FIG. 7, anti-hNGF MAbs inhibit binding of hNGF to the p75-IgG receptor immunoadhesin using $^{125}$I-labeled hNGF. MAbs 911, 912 and 938 shows the highest inhibitory activity with 75-90% reduction in binding observed in the presence of less than 1 nM of MAb. MAb 909 also showed potent blocking ability (>90% inhibition with 10 nM MAb), while MAbs 908 and 14.14 were significantly less potent (FIG. 7).

B. Kinase-Induced Receptor Activation (KIRA) Assay.

Figure 8:
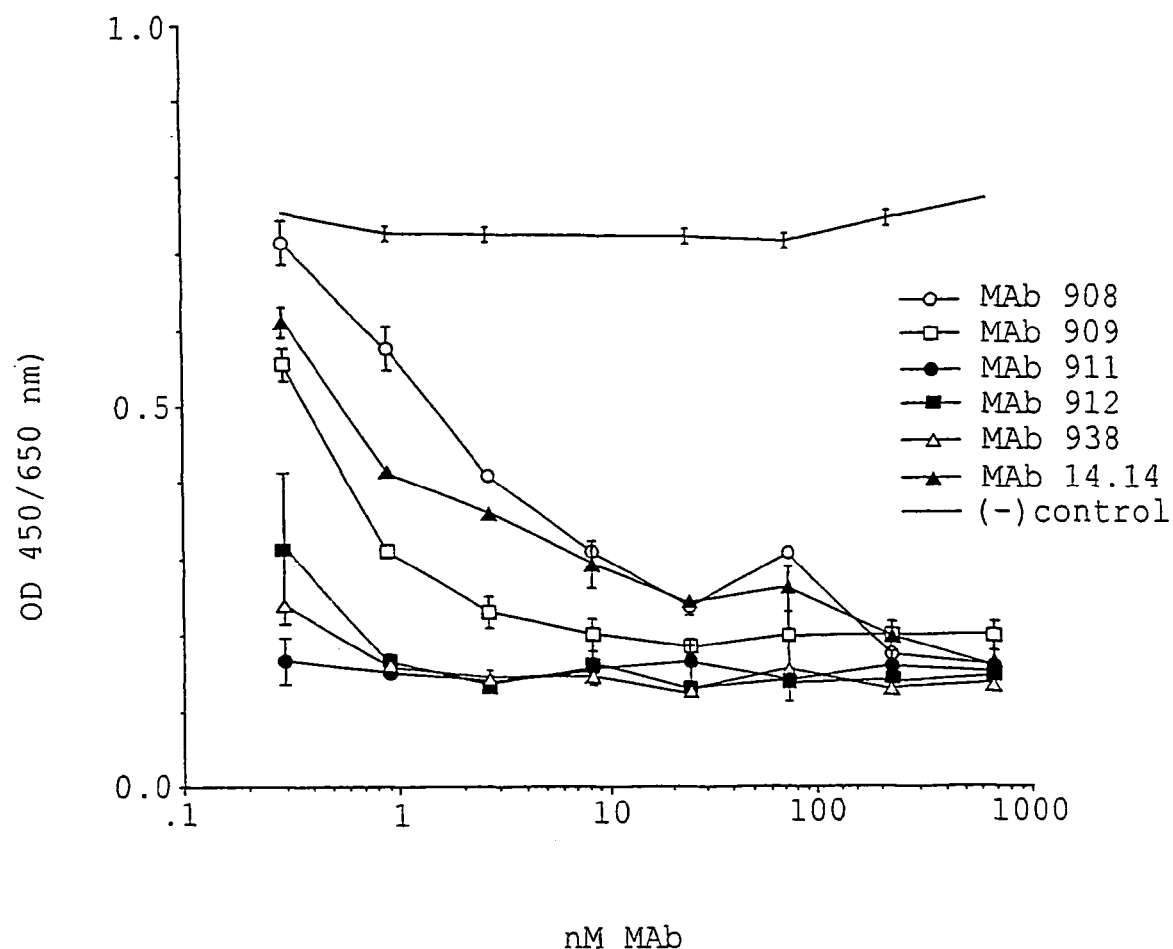

A kinase-induced receptor activation (KIRA) assay was used to measure NGF-dependent TrkA autophosphorylation in transfected cells in response to stimulation with a ligand, such as hNGF, and/or agonist monoclonal antibodies (Sadick at al., *Exp. Cell Res.* 234:354-361 (1997)). The anti-NGF MAbs were evaluated for their ability to inhibit the binding of hNGF to the TrkA extracellular domain expressed on CHO transfected cells and the subsequent phosphorylation of tyrosine residues on TrkA (FIG. 8). Phosphorylation of tyrosine residues was measured by ELISA using an antiphosphotyrosine MAb.

Microtiter plates (Costar, Cambridge, Md.) were coated with 1×10$^5$ chinese hamster ovary (CHO) cells expressing the extra-cellular domain of the TrkA receptor with a Herpes simplex virus glycoprotein D fragment (gD), a 26 amino acid polypeptide serving as an epitope tag. Samples of either hNGF alone (150 pM) (as a positive control) or hNGF (150 pM final) preincubated overnight at 4° C. with the individual anti-NGF MAbs (667 nM 0.31 nM final) were then added to wells containing the TrkA expressing CHO cells (50 L per well) and incubated at 37° C. for 25 minutes. An irrelevant monoclonal antibody not directed against NGF was used as a negative control. The hNGF-stimulated cells were then treated with lysis buffer, and the lysates were processed in gD-MAb-coated microtiter plates for the ELISA detection of TrkA-containing phosphotyrosine similar to the procedure described by Sadick et al (Sadick et al., *Anal. Biochem.*, 235:207-214 (1996)). 100 l of biotinylated 4G10 (monoclonal anti-phosphotyrosine from Upstate Biologicals, Inc. (UBI, Lake Placid, N.Y.)) diluted to 0.2 mg/ml in dilution buffer (PBS containing 0.5% BSA, 0.05% Tween 20, 5 mM EDTA, and 0.01% thimerosol) was added to each well. After incubation for 2 hours at room temperature the plate was washed and 100 l HRP-conjugated streptavidin (Zymed Laboratories, S. San Francisco, Calif.) diluted 1:50000 in dilution buffer was added to each well. The plate was incubated for 30 minutes at room temperature with gentle agitation. The free avidin conjugate was washed away and 100 l freshly prepared substrate solution (tetramethyl benzidine, TMB, two-component substrate kit, Kirkegard and Perry, Gaitehersbug, Md.) was added to each well. The reaction was allowed to proceed for 10 minutes, after which the color development was stopped by the addition of 100 l/well of 1.0 M $H_3PO_4$. The absorbance at 450 nm was read with a reference wavelength of 650 nm ($A_{450/460}$), using a Vmax plate reader (Molecular Devices, Palo Alto, Calif.) controlled with a Macintosh Centris 650 (Apple Computers, Cupertino, Calif.) and DeltaSoft software (BioMetallics, Inc., Princeton, N.J.).

As shown in FIG. 8, all the selected anti-NGF monoclonal antibodies could inhibit both the binding of hNGF to the TrkA extracellular domain expressed on CHO transfected cells and phosphorylation of tyrosine residues of the TrkA receptor. Preincubation of hNGF with MAbs 911, 912 and 938 at the lowest concentration tested (0.3 nM) resulted in approximately 60-80% maximal inhibition of tyrosine phosphorylation relative to the control MAb. MAbs 908, 909 and 14.14 were less potent.

C. Embryonic Rat Dorsal Root Ganglion Survival Bioassay.

Another assay used to determine the effects of anti-NGF monoclonal antibodies on NGF-dependent processes was the embryonic rat E14 dorsal root ganglia (DRG) survival bioassay. Anti-NGF monoclonal antibodies were evaluated for their ability to inhibit the survival effects of hNGF on embryonic rat E14 dorsal root ganglia (DRG) neurons (FIG. 9).

Dorsal root ganglion (DRG) neurons obtained from E15 rats (six to eight embryos) were cultured in F12 media with additives (McMahon et al., *Nat. Med.* 8:774-780 (1995)) and 3 ng/mL of hNGF either with or without anti-NGF monoclonal antibodies. After 72 hours of incubation at 37° C., the cells were fixed with formaldehyde and viable neurons were counted.

Figure 9:
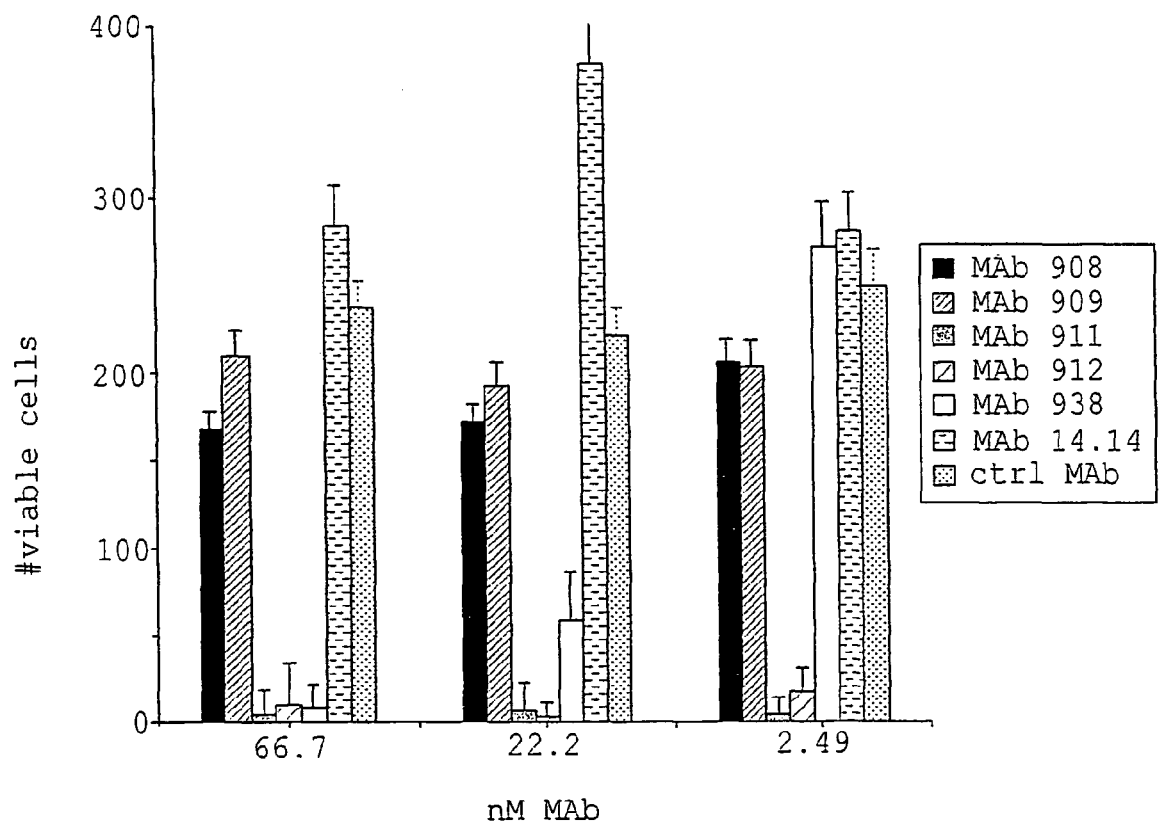

FIG. 9 shows the inhibition of DRG neuronal survival by anti-NGF monoclonal antibodies. While MAbs 908, 909 and 14.14 reduced the survival by only 20-30% at the highest concentration (67 nM; 10 g/ml), MAbs 911 and 912 inhibited greater than 90% survival at approximately 30-80 fold lower concentrations (0.8-2.4 nM; 0.12-0.37 g/ml). MAb 938 was able to inhibit survival activity by 90%, but was 10-30 fold less potent than MAbs 911 and 912.

Figure 3D:
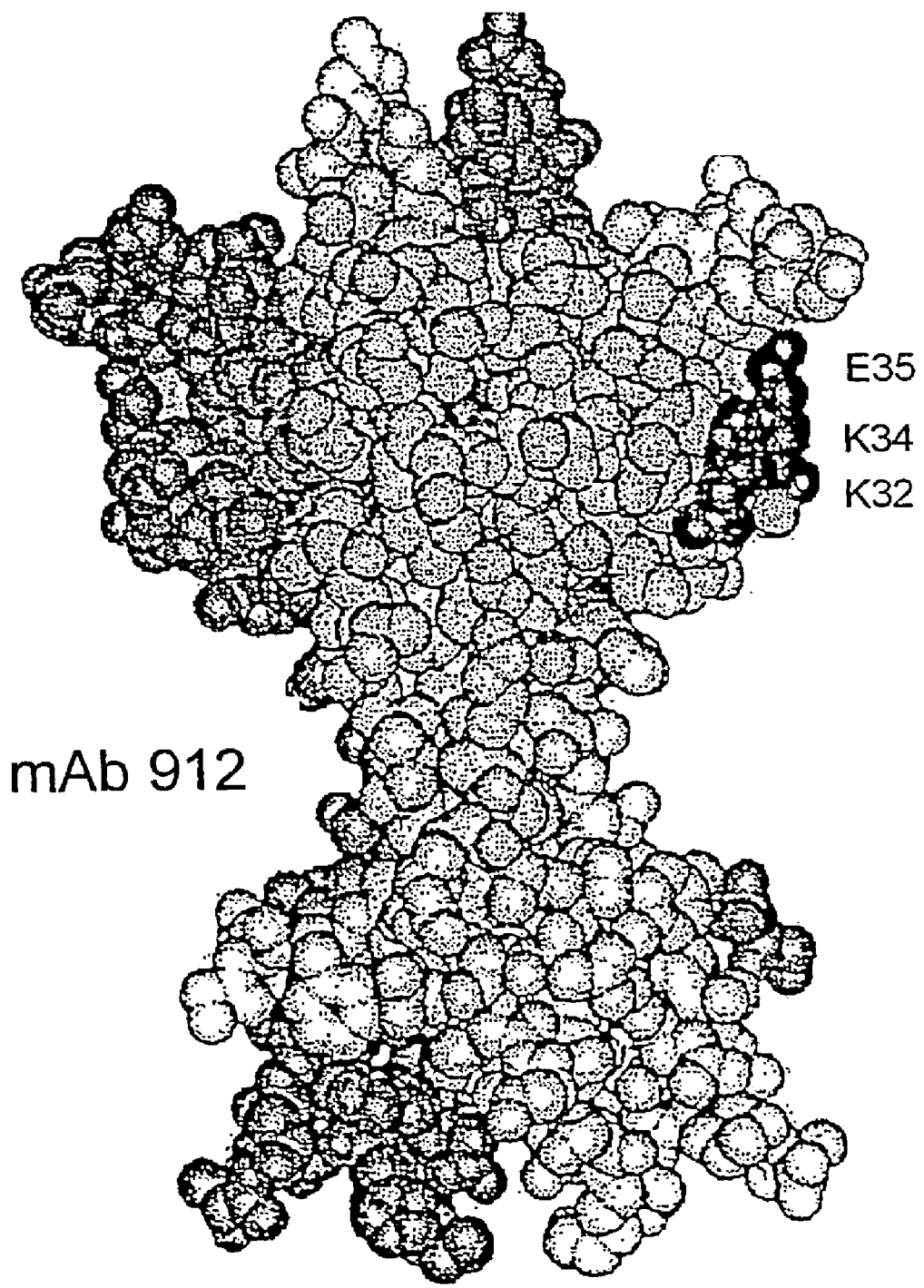
Figure 3E:
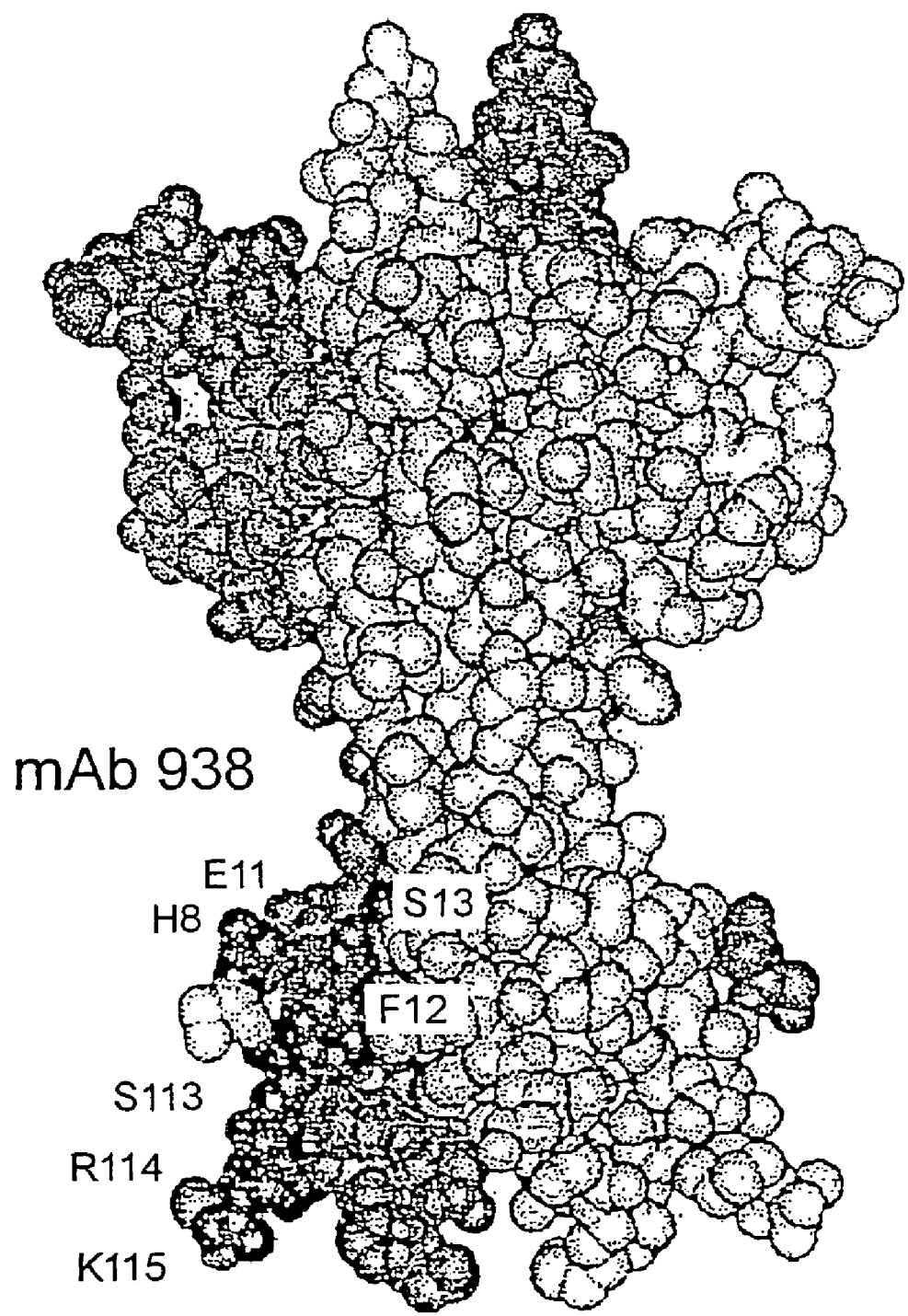
Figure 3F:
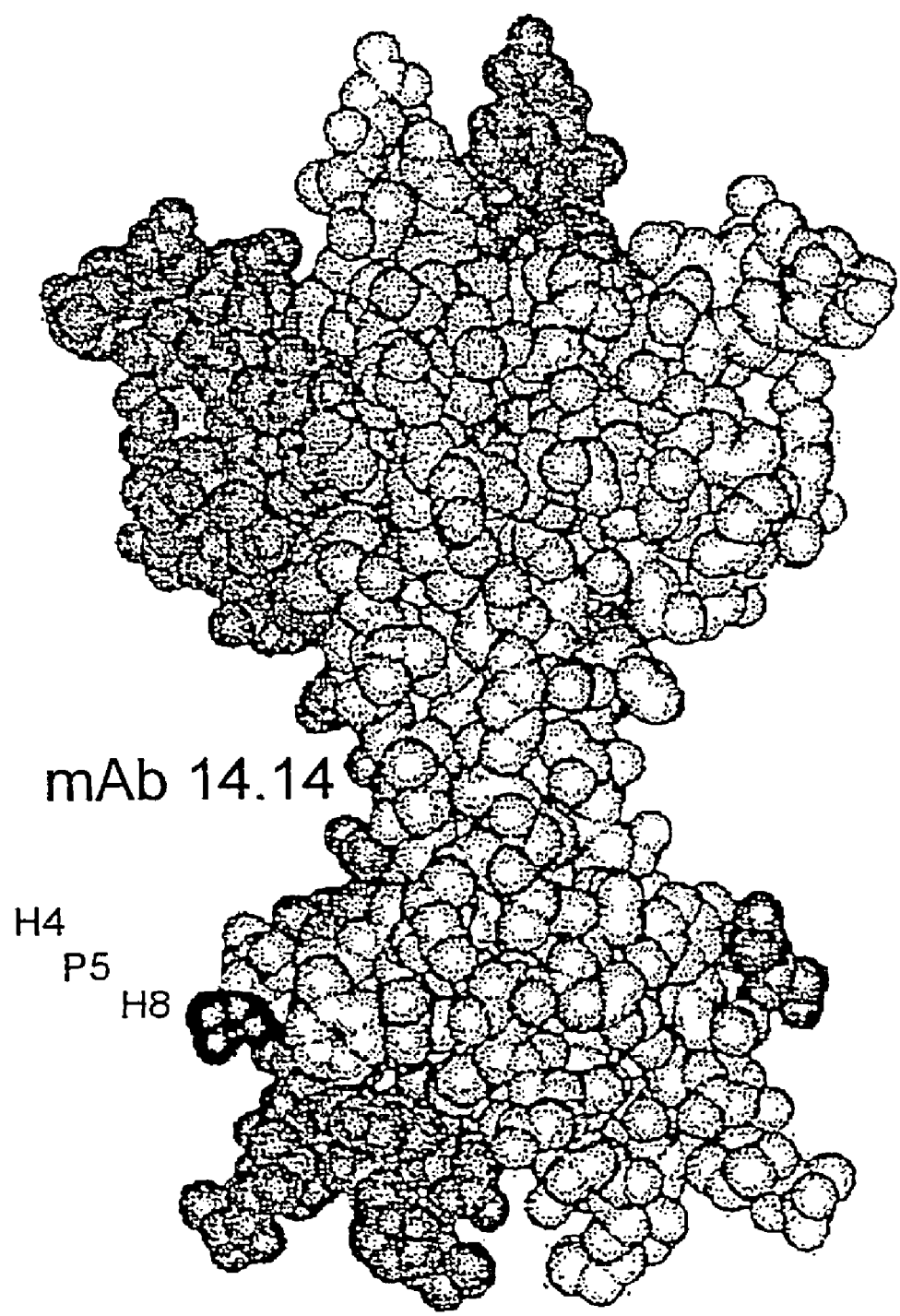
Figure 4A:
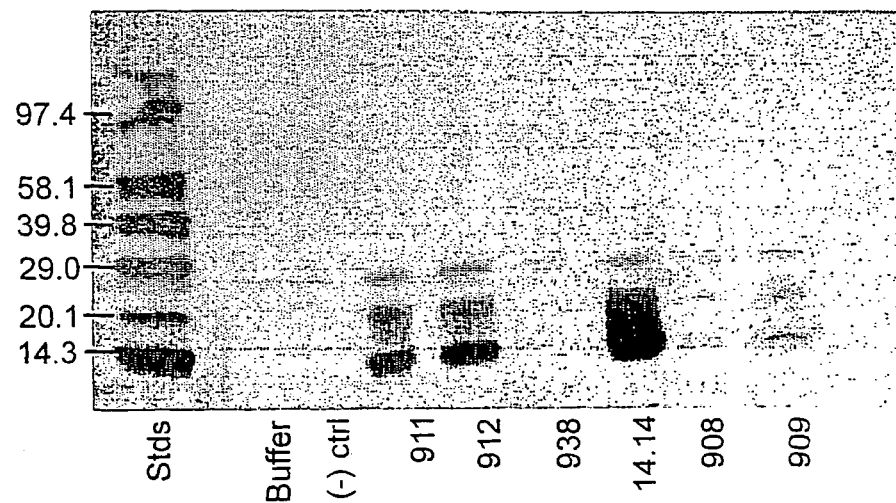
Figure 4B:
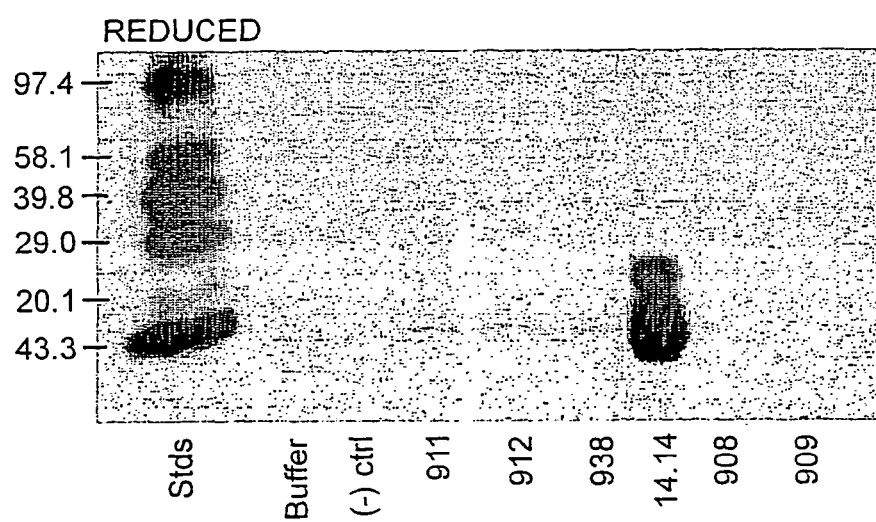

MAb 911 was the most potent blocker of the NGF/TrkA interaction. MAb 911 recognizes an epitope containing the overlapping NGF-TrkA and p75 binding region-turn A'-A" (V-1) and the dominant TrkA binding region in-sheet (FIG. 3D). The second strongest NGF/TrkA inhibitor, MAb 912, recognizes the residues K32, K34 and K35, a region previously shown to be crucial for the NGF/p75 interaction. MAb 938, another potent blocker of TrkA and p75 binding also recognizes regions critical for TrkA or p75 binding, the N- and C-termini.

The observed differences in antibody blocking specificity are not due to the relative affinities of the MAbs toward hNGF because two of the three most potent blocking antibodies (911 and 938) have lower affinities for NGF than the weaker blocking MAbs.

NGF regions critical for binding to MAbs 911 and 912 overlap with regions identified as critical regions for TrkA and p75 binding. MAbs 911 and 912 are capable blockers of NGF-induced activities, indicating that these would be specific antagonists of in vivo activities such as inflammatory hyperalgesia.

Example 3

The Effect of Anti-NGF on the Immune Response

Figure 10:
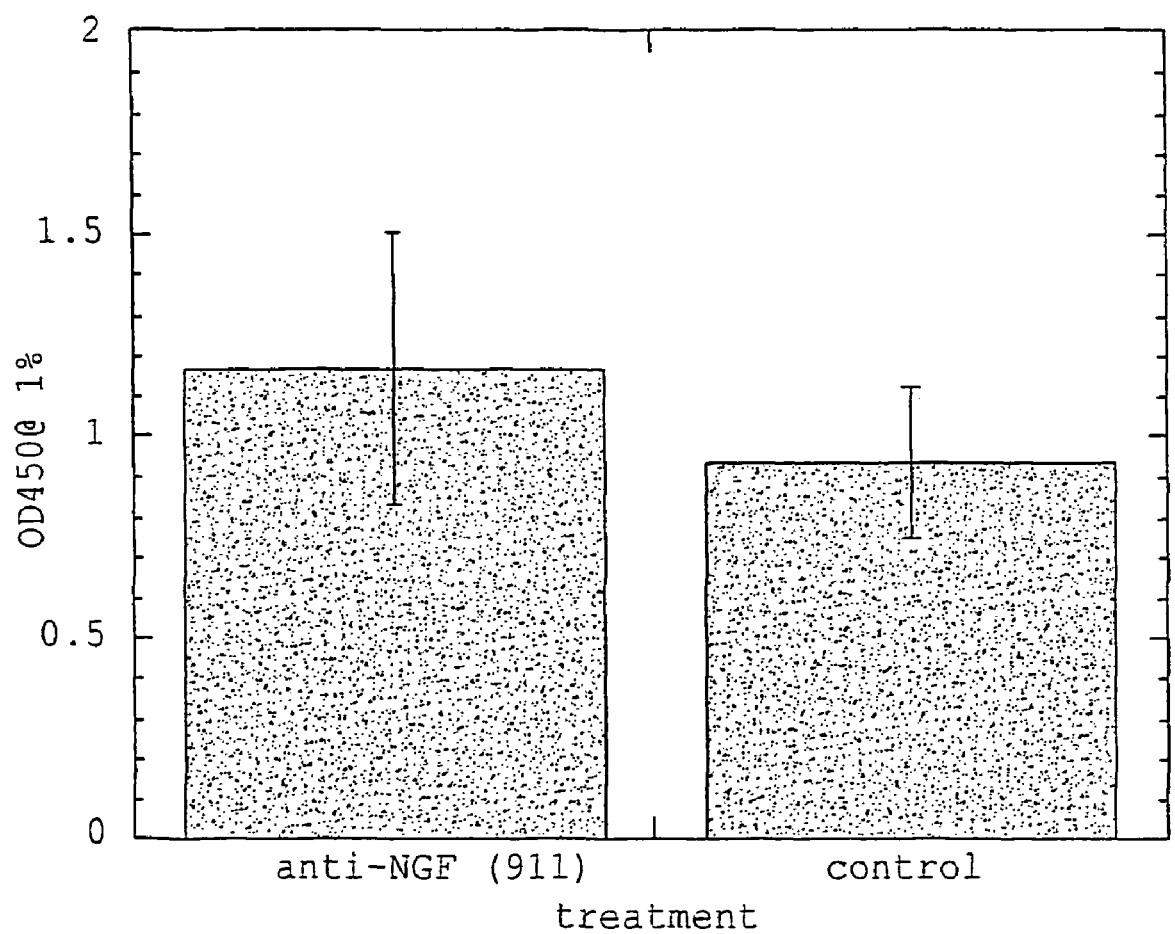

Mice were immunized subcutaneously with 10 g ovalbumin on day 0 and allowed to recover. On day 40 following immunization animals were injected IP with 10 mg/kg anti-NGF antibody 911 or a control, isotype matched antibody. Two days later animals were boosted with ovalbumin. The immune response was measured by ELISA on serum samples taken on day 47. As can be seen in FIG. 10, there was no significant ($p>0.05$) difference in the immune response between the animals receiving anti-NGF antibody 911 and animals receiving the control antibody. However, there was a non-significant trend towards an increase in the immune response in animals treated with the anti-NGF monoclonal antibody.

Figure 11:
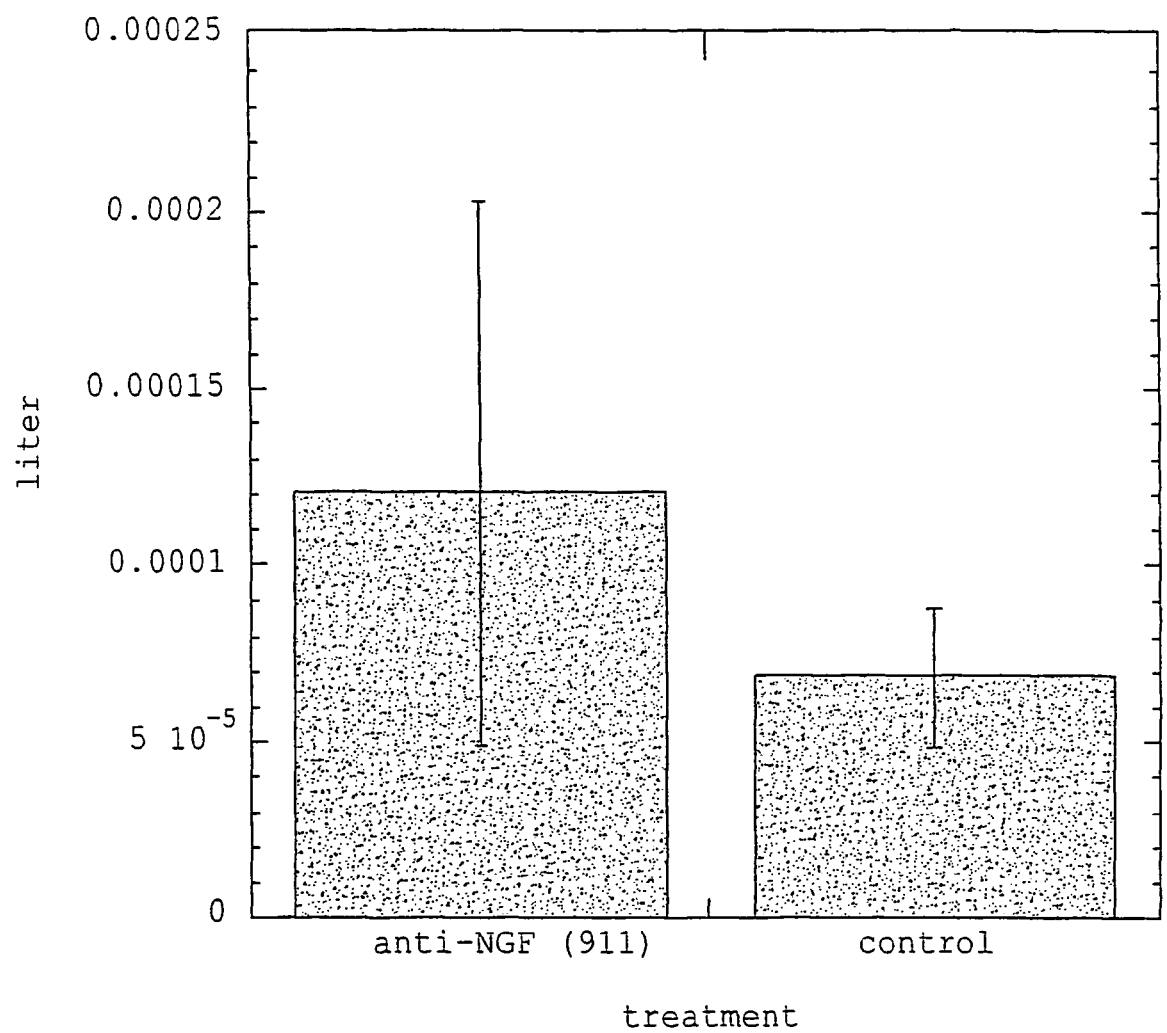

By contrast, FIG. 11 shows that following immunization with chicken gamma-globulin, treatment with anti-NGF produces a non-significant trend toward a decrease in the immune response. Animals were immunized with 10 g of chicken gamma-globulin on day 0 and treated with anti-NGF antibody 911 or a control, isotype matched antibody (10 mg/kg IP) on day 40. On day 42 animals were boosted with gamma-globulin and on day 47 serum samples were taken and analyzed by ELISA. There was no significant difference ($p>0.05$) in the immune response between the two groups. However there was a trend towards a decrease in the immune response following treatment with anti-NGF monoclonal antibody 911.

Example 4

Effect of Anti-NGF Monoclonal Antibodies on Hyperalgesia

The effect of anti-NGF antibodies on NGF induced thermal hyperalgesia was investigated. Briefly, adult Fischer female rats were trained for two sessions a day with the Hargreaves' test for at least two days prior to treatment. After familiarization with the apparatus and protocol, animals were randomly assigned to the control or experimental group. Both groups were tested for baseline responsiveness and then given intraplantar injections in one paw in a volume of 50 l under isofluorane anaesthesia. The injections in each group contained 1.25% carrageenan, in combination with either 90 g of anti-NGF antibody or an indifferent, isotype matched control antibody.

Figure 12:
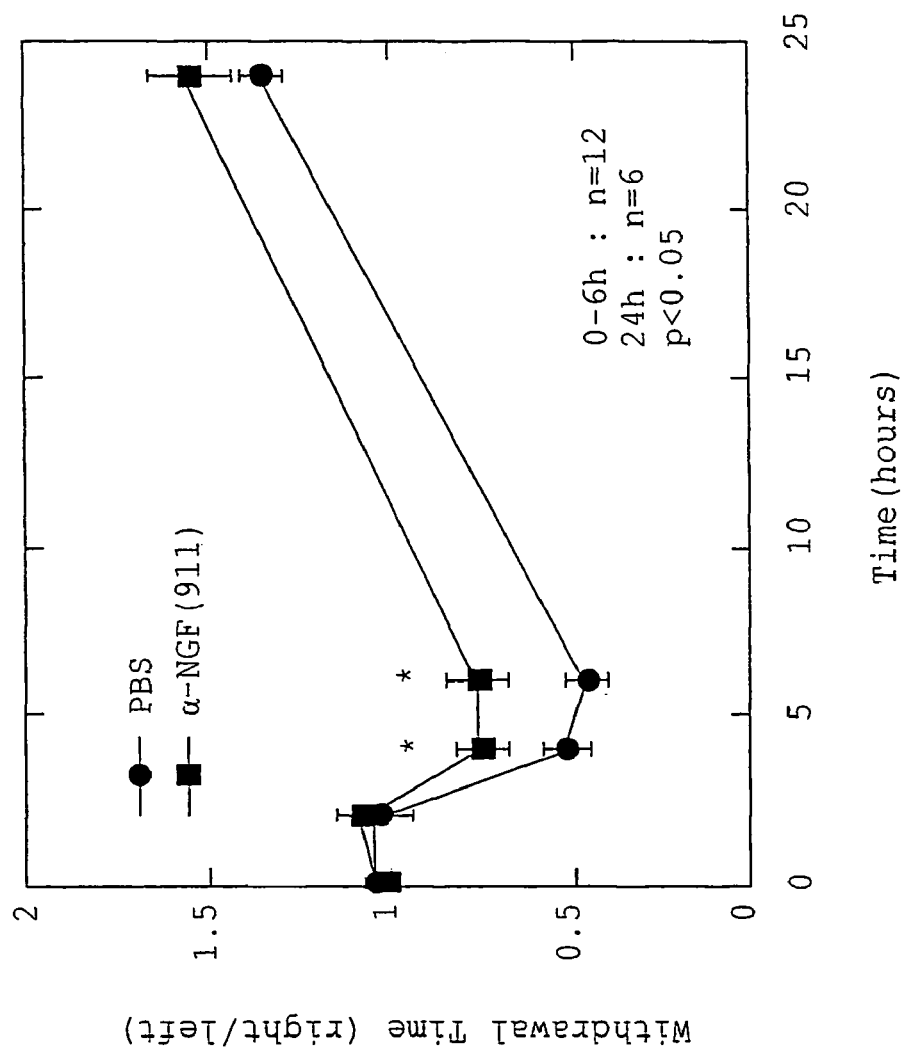

Thermal withdrawal latencies were measured at 0, 2, 4, 6 and 24 hours post injection by the Hargreaves' test. As shown in FIG. 12, at 4 and 6 hours after treatment the thermal hyperalgesia that follows carageenan injection was significantly decreased in animals treated with anti-NGF monoclonal antibody 911 compared to control animals.

Example 5

Effect of Anti-NGF Monoclonal Antibodies on Response to Allergens

Male C57/BL6 mice (Jackson Laboratories) were treated with either monoclonal anti-NGF antibody 911 (n=16) or an isotype matched anti-gD control antibody (clone 1766; n=16). On day-1, animals were treated with 20 mg/kg of antibody and on days 6, 13, 20 and 22 they were treated with 10 mg/kg of antibody. All antibody treatments were subcutaneously injected into the scruff of the neck.

On days 0 and 14 half of the mice in each group were sensitized (SN) by intraperitoneal injection of 30 AU of dust mite antigen (DMA; diluted with Dulbecco's PBS and then 1:2 with ALUM, as an adjuvant, for a final concentration of 300 AU/ml). The non-sensitized mice (NS) received an equal volume of Dulbecco's PBS diluted 1:2 with ALUM as a control.

Mice were then challenged with inhaled dust mite antigen (DMA) on days 21 and 22. Dust mite was diluted to 6000 AU/ml using Dulbecco's PBS plus 0.01% Tween-20 for aerosolizaton. All inhalation challenges were administered in a Plexiglas pie exposure chamber. DMA was aerosolized using a PARI IS-2 nebulizer driven at 22 PSI. The nebulizer was filled with 3 ml and run to completion (30 min.). Total deposited dose/exposure into the lung was ~6.5 AU DMA.

Mice were assessed for airway hyperreactivity, cellular infiltration into the broncheolar lavage (BAL) fluid, cytokine levels in BAL, and serum titer against dust mite as well as serum IgE levels. Briefly, on day 24, 48 hours after the last challenge, mice were anesthetized, catheterized in the jugular vein and tracheotomized. Miche were then paralyzed with 0.28 mg/kg pancuronium and loaded into a Plexiglas flow plethysmograph for measurement of thoracic expansion and airway pressure. Mice were ventilated using 100% oxygen at a frequency of 170 bpm and Vt equal to 9 l/g. Breathing mechanics (lung resistance and dynamic compliance) were continuously monitored using the Buxco XA data acquisition program. Mice were given a volume history (5 breaths at 2.5×Vt), allowed to stabilize for 2 min before baseline measurement, and then given a one-time 5 second dose of the agonist at a body weight adjusted flow rate using a Harvard syringe pump and syringe application software.

Blood (serum), BAL and lungs were collected. Serum was assayed for total and specific IgE and IgG. BAL was obtained by injecting the same aliquot of NaCl 3 times and was assayed for total IgE by ELISA. Total white blood cells and cell differentials were obtained from BAL cells.

Figure 13:
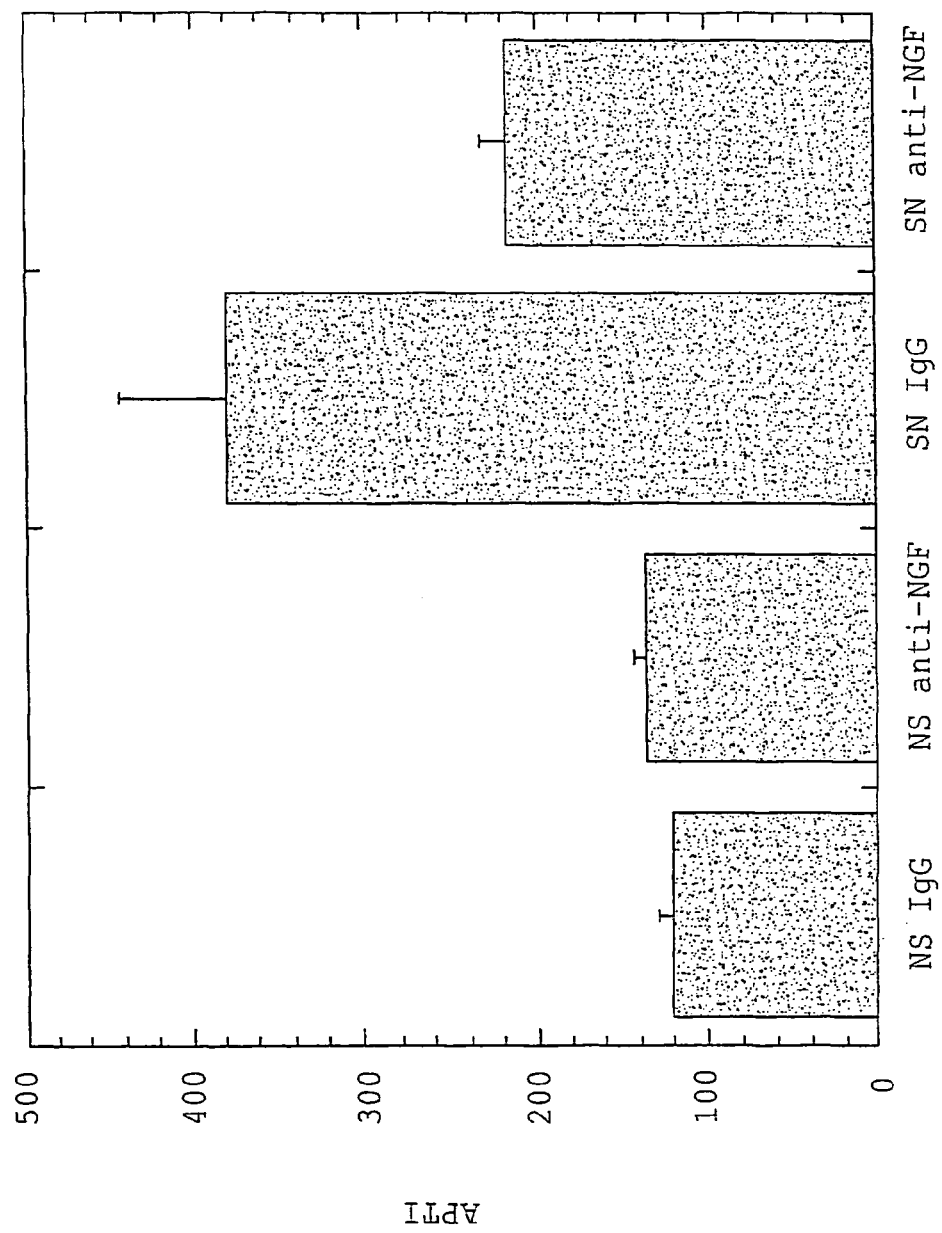
Figure 14:
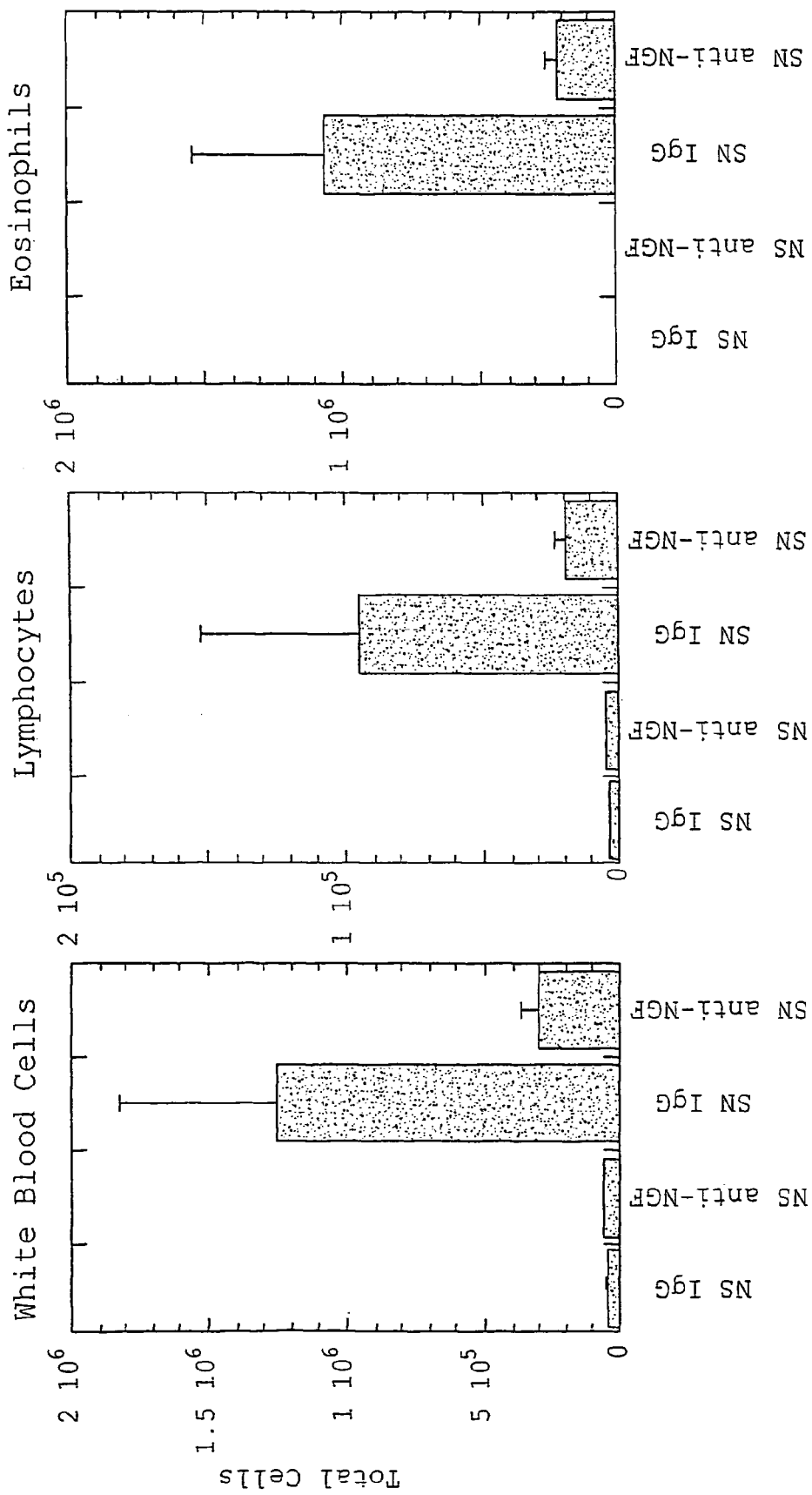
Figure 15:
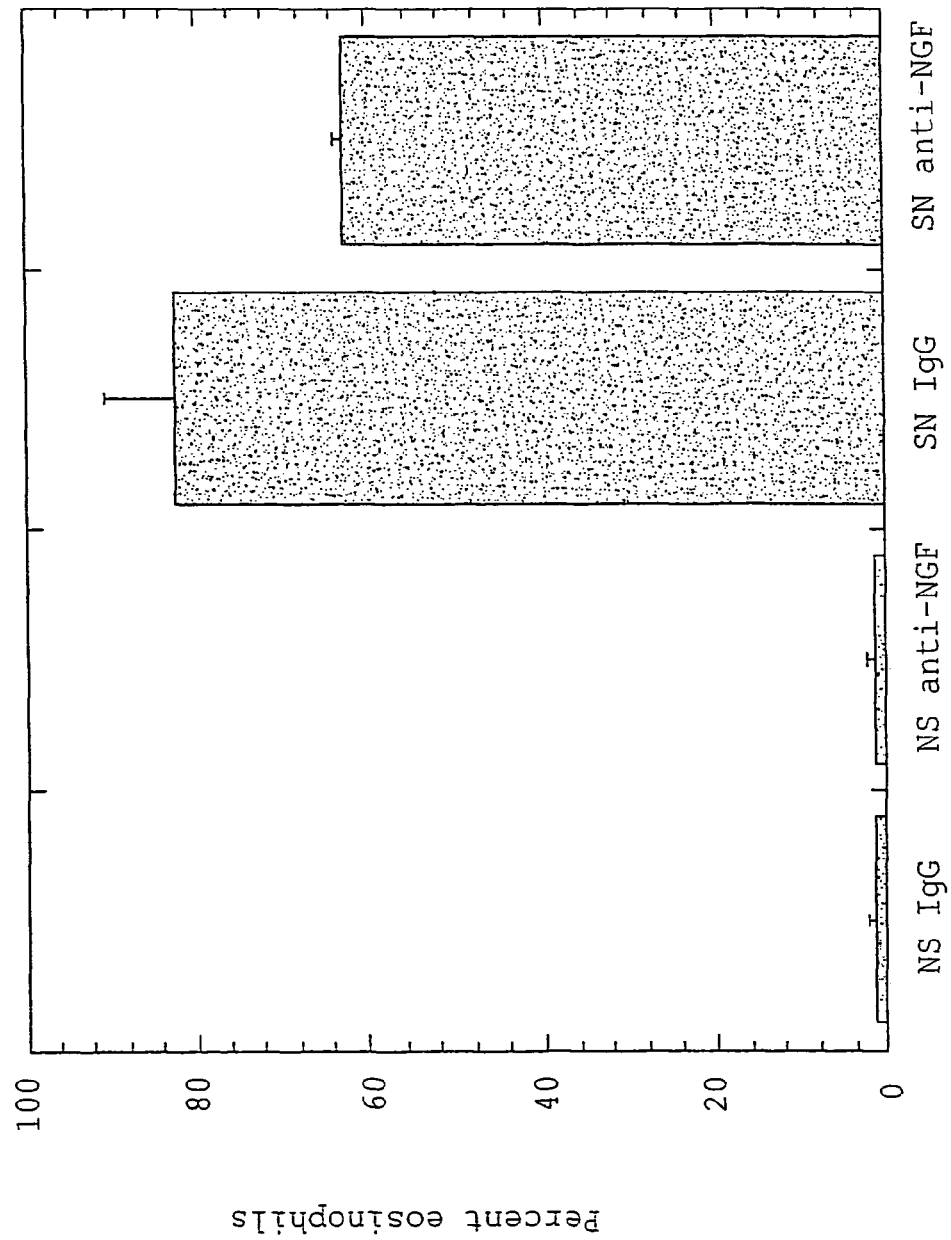
Figure 16:
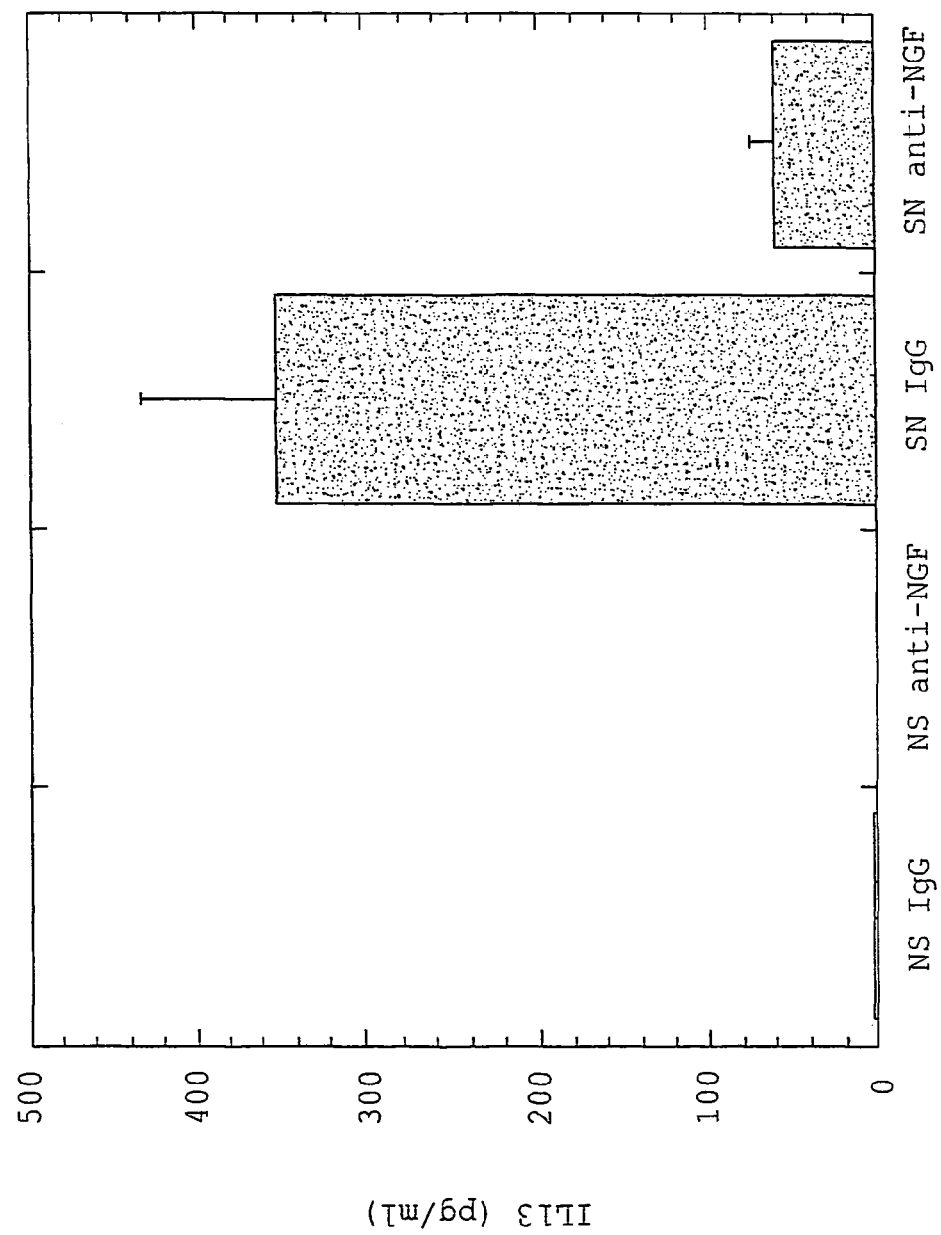

Treatment with anti-NGF monoclonal antibody caused a significant drop in airway hyperreactivity (FIG. 13), as well as in inflammation as measured by cellular infiltration into the BAL (FIG. 14). However, there is still a very high proportion of eosinophils in BAL from anti-NGF treated animals (FIG. 15). Anti-NGF antibody treatment also decreased the level of the Th2 cytokine IL-13 in the BAL (FIG. 16).

Figure 18:
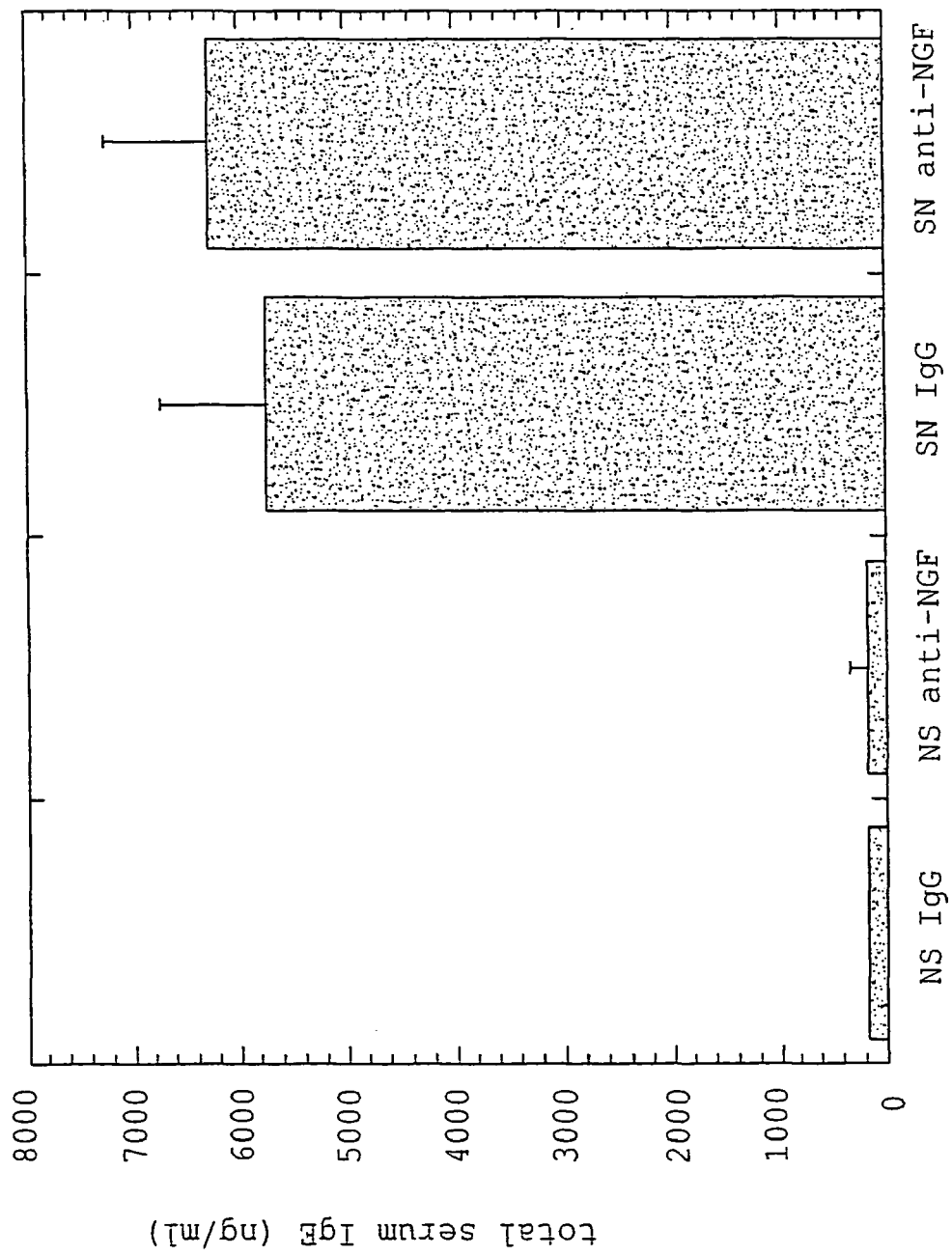

Despite its ability to decrease the inflammatory response to allergen, anti-NGF antibody treatment did not decrease the humoral immune response to dust mite, either as measured by the total serum immunoglobulin titer to dust mite (FIG. 17) or by the serum level of IgE (FIG. 18). This indicates that the antibody did block the biological effect of NGF, but did not affect the survival or function of B-lymphocytes.

Figure 19:
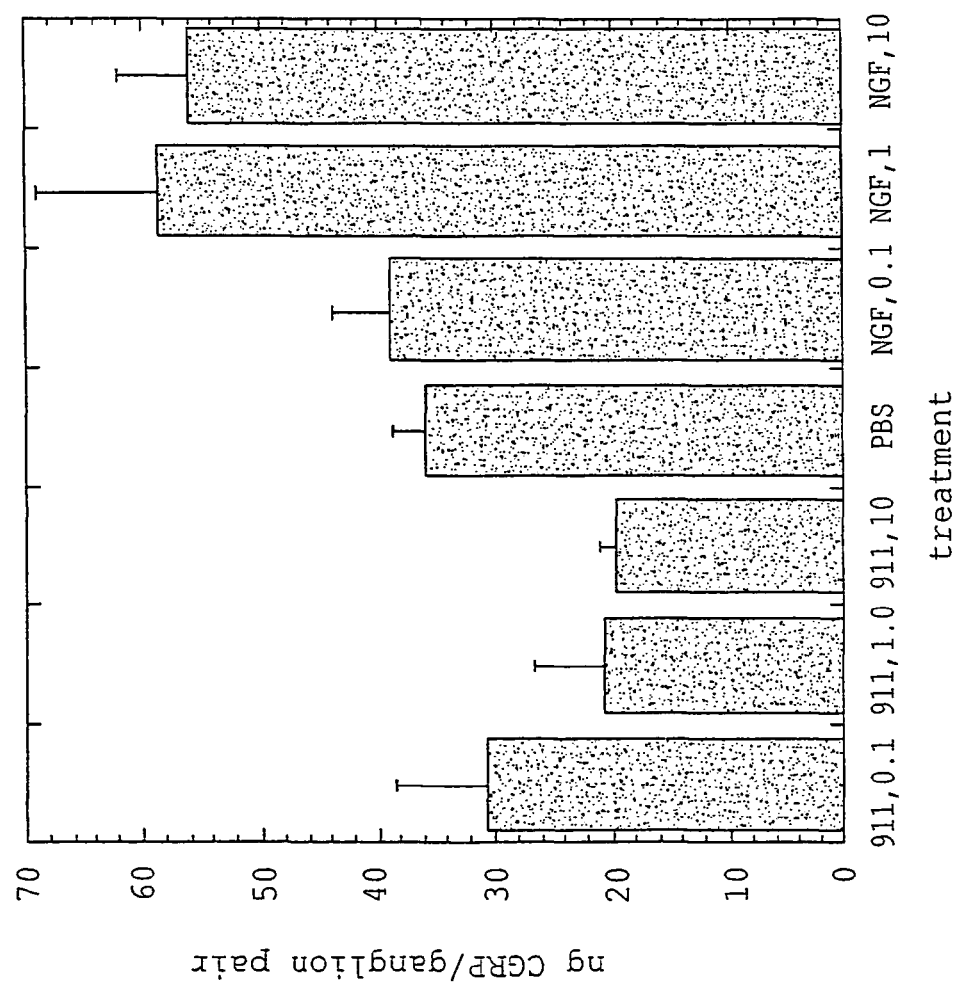

To confirm that the anti-NGF antibody 911 was having a functionally significant effect on NGF, a parallel experiment was carried out in which mice were injected subcutaneously in the scruff of the neck with 0.1, 1 or 10 mg/kg of anti-NGF monoclonal antibody 911 on days 1 and 8, or with NGF at 0.1, 1 or 10 mg/kg on days 1, 3, 6 and 8. Animals were sacrificed on day 0.9 and examined for the level of the neuropeptide CGRP in the trigeminal ganglion. Treatment with 1 or 10 mg/kg of NGF caused an increase in CGRP, verifying that this peptide is regulated by NGF levels (FIG. 19). Treatment with 1 or 10 mg/kg of anti-NGF monoclonal antibody 911 caused a decrease in the CGRP content of the ganglion (FIG. 19), verifying that this dose produces a functionally significant blockade of endogenous NGF at the time when the immune response was occurring in the experiment described above.

Deposit of Biological Material

The following hybridoma cell lines have been deposited with the American Type Culture Collection, 10801 University Boulevard, Manassas Va. 20110-2209, USA (ATCC):

| Antibody Designation | ATCC No. | Deposit Date |
|---|---|---|
| MAb911 | ATCC Accession No. PTA-9141 | Apr. 9, 2008 |
| MAb912 | ATCC Accession No. PTA-9142 | Apr. 9, 2008 |
| MAb938 | ATCC Accession No. PTA-9143 | Apr. 9, 2008 |

This deposit was made under the provisions of the Budapest Treaty on the International Recognition of the Deposit of Microorganisms for the Purpose of Patent Procedure and the Regulations thereunder (Budapest Treaty). This assures maintenance of viable cultures for 30 years from the date of the deposit. The organisms will be made available by ATCC under the terms of the Budapest Treaty, and subject to an agreement between Genentech, Inc. and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.12 with particular reference to 886 OG 638).

The assignee of the present application has agreed that if the cultures on deposit should die or be lost or destroyed when cultivated under suitable conditions, they will be promptly replaced on notification with a viable specimen of the same culture. Availability of the deposited strain is not to be construed as a license to practice the invention in contravention of the rights granted under the authority of any government in accordance with its patent laws.

What is claimed is:

1. A method of controlling pain, thermal hyperalgesia and airway hyperreactivity in a human patient suffering therefrom without significantly adversely affecting the immune system of said patient, comprising administering to said patient an effective amount of an anti-human NGF (anti-hNGF) monoclonal antibody capable of binding hNGF with an affinity in the nanomolar or sub-nanomolar range, and inhibiting the binding of hNGF to human TrkA (hTrkA) in vivo, wherein said anti-hNGF monoclonal antibody is selected from MAb911 (ATCC Accession No. PTA-9141), MAb911 variants comprising a different glycosylation pattern, MAb911 chimeric antibodies, monoclonal antibodies that bind the same hNGF epitope as MAb911 and antigen-binding fragments of said antibodies, and wherein said anti-hNGF monoclonal antibody has no significant adverse effect on the immune system of said patient.

2. The method of claim 1 wherein the binding affinity of said antibody to hNGF is about 0.10 to about 0.80 nM.

3. The method of claim 2 wherein the binding affinity of said antibody to hNGF is about 0.15 to about 0.75 nM.

4. The method of claim 2 wherein the binding affinity of said antibody to hNGF is about 0.18 to about 0.72 nM.

5. The method of claim 1 wherein said antibody is also able to bind murine NGF (muNGF).

6. The method of claim 1 wherein said antibody is chimeric.

7. The method of claim 1 wherein said antibody is humanized.

8. The method of claim 1 wherein said antibody is human.

9. The method of claim 1 wherein said antibody is administered in combination with another therapeutic agent.

10. The method of claim 1 wherein said antibody is administered in combination with a corticosteroid.

11. The method of claim 10 wherein said corticosteroid is beclomethasone diproprionate (BDP).

12. The method of claim 1, wherein said pain is chronic pain.

* * * * *

UNITED STATES PATENT AND TRADEMARK OFFICE
CERTIFICATE OF CORRECTION

PATENT NO. : 7,727,527 B2  Page 1 of 1
APPLICATION NO. : 10/479872
DATED : June 1, 2010
INVENTOR(S) : David L. Shelton It is certified that error appears in the above-identified patent and that said Letters Patent is hereby corrected as shown below:

Cover Page, Title item (54): should read as follows:

~~ANTI-NGF ANTIBODIES FOR THE THERAPEUTIC TREATMENTS,~~ <u>ANTI-NGF ANTIBODIES FOR THE TREATMENT OF VARIOUS DISORDERS</u>

Signed and Sealed this
Twenty-first Day of June, 2011

David J. Kappos
*Director of the United States Patent and Trademark Office*

UNITED STATES PATENT AND TRADEMARK OFFICE
CERTIFICATE OF CORRECTION

PATENT NO.         : 7,727,527 B2                                    Page 1 of 1
APPLICATION NO.    : 10/479872
DATED              : June 1, 2010
INVENTOR(S)        : David L. Shelton It is certified that error appears in the above-identified patent and that said Letters Patent is hereby corrected as shown below:

Cover Page, Title item (54) and at Column 1, lines 1 and 2, title, should read as follows:

~~ANTI-NGF ANTIBODIES FOR THE THERAPEUTIC TREATMENTS,~~ ANTI-NGF ANTIBODIES FOR THE TREATMENT OF VARIOUS DISORDERS

This certificate supersedes the Certificate of Correction issued June 21, 2011.

Signed and Sealed this
Twenty-sixth Day of July, 2011

David J. Kappos
*Director of the United States Patent and Trademark Office*